(12) United States Patent
Vila et al.

(10) Patent No.: US 8,632,591 B2
(45) Date of Patent: Jan. 21, 2014

(54) NUCLEUS PROSTHESES

(75) Inventors: Thierry Vila, Paris (FR); Henry Dufour, Marseilles (FR); Jérôme Allain, Bagnolet (FR)

(73) Assignee: LDR Medical, Rosières Près Troyes (FR)

( * ) Notice: Subject to any disclaimer, the term of this patent is extended or adjusted under 35 U.S.C. 154(b) by 792 days.

(21) Appl. No.: 11/874,144

(22) Filed: Oct. 17, 2007

(65) Prior Publication Data

US 2008/0312743 A1 Dec. 18, 2008

(30) Foreign Application Priority Data

Jun. 15, 2007 (FR) ...................................... 07 04326

(51) Int. Cl.
*A61F 2/44* (2006.01)

(52) U.S. Cl.
USPC .................................... 623/17.11; 623/17.16

(58) Field of Classification Search
USPC .......................................... 623/17.11–17.16
See application file for complete search history.

(56) References Cited

U.S. PATENT DOCUMENTS

| | | | |
|---|---|---|---|
| 4,865,606 A | 9/1989 | Rehder | |
| 5,033,607 A | 7/1991 | Rivera | |
| 5,171,280 A | 12/1992 | Baumgartner | |
| 5,192,326 A | 3/1993 | Bao et al. | |
| 5,320,644 A | 6/1994 | Baumgartner | |
| 5,480,442 A | 1/1996 | Bertagnoli | |
| 5,534,023 A | 7/1996 | Henley | |
| 5,556,431 A | 9/1996 | Buttner-Janz | |
| 5,562,736 A | 10/1996 | Ray et al. | |
| 5,702,391 A | 12/1997 | Lin | |
| 5,702,454 A | 12/1997 | Baumgartner | |
| 5,755,797 A * | 5/1998 | Baumgartner | 623/17.16 |
| 5,824,093 A | 10/1998 | Ray et al. | |
| 6,006,458 A | 12/1999 | Weiss | |
| 6,022,376 A | 2/2000 | Assell | |
| 6,093,205 A | 7/2000 | McLeod et al. | |
| 6,110,210 A | 8/2000 | Norton et al. | |
| 6,273,914 B1 | 8/2001 | Papas | |

(Continued)

FOREIGN PATENT DOCUMENTS

| | | |
|---|---|---|
| DE | 3726969 | 3/1989 |
| DE | 9304368 | 5/1993 |

(Continued)

OTHER PUBLICATIONS

Implant for Osseous Anchoring with Polyaxial Head, U.S. Appl. No. 10/498,234, filed Dec. 7, 2004.

(Continued)

*Primary Examiner* — David Bates
(74) *Attorney, Agent, or Firm* — Denko Coburn Lauff LLP

(57) ABSTRACT

An nucleus prosthesis is disclosed having a plurality of linked segments configured to form, in a closed position, a disc shape. A method includes inserting a plurality of linked segments into an annulus fibrosus and closing the prosthesis so that a first segment inserted into the annulus fibrosus and a last segment inserted into the annulus fibrosus are substantially abutted. Another method includes inserting a plurality of linked segments into an intervertebral disc space and closing the prosthesis so that a first segment inserted into the intervertebral disc space and a last segment inserted into the intervertebral disc space are substantially abutted.

27 Claims, 15 Drawing Sheets

(56) References Cited

U.S. PATENT DOCUMENTS

| | | | |
|---|---|---|---|
| 6,387,130 B1 * | 5/2002 | Stone et al. | 623/17.16 |
| 6,482,234 B1 | 11/2002 | Weber et al. | |
| 6,579,291 B1 | 6/2003 | Keith et al. | |
| 6,602,291 B1 | 8/2003 | Ray et al. | |
| 6,620,196 B1 | 9/2003 | Trieu | |
| 6,689,125 B1 | 2/2004 | Keith | |
| 6,726,721 B2 | 4/2004 | Stoy et al. | |
| 6,830,570 B1 | 12/2004 | Frey et al. | |
| 6,893,466 B2 | 5/2005 | Trieu | |
| 7,037,340 B2 | 5/2006 | Gau | |
| 7,056,344 B2 | 6/2006 | Huppert et al. | |
| 7,198,047 B2 | 4/2007 | Lambrecht et al. | |
| 7,258,700 B2 | 8/2007 | Lambrecht et al. | |
| 7,291,170 B2 | 11/2007 | Huppert | |
| 7,326,250 B2 | 2/2008 | Beaurain et al. | |
| 7,351,262 B2 * | 4/2008 | Bindseil et al. | 623/17.16 |
| 7,494,508 B2 | 2/2009 | Zeegers | |
| 7,507,248 B2 | 3/2009 | Beaurain et al. | |
| 7,524,333 B2 | 4/2009 | Lambrecht et al. | |
| 7,563,282 B2 | 7/2009 | Lambrecht et al. | |
| 7,591,853 B2 * | 9/2009 | Felt et al. | 623/17.16 |
| 7,594,931 B2 | 9/2009 | Louis et al. | |
| 7,618,461 B2 | 11/2009 | Trieu | |
| 7,628,814 B2 | 12/2009 | Studer et al. | |
| 7,632,282 B2 | 12/2009 | Dinville | |
| 7,682,396 B2 | 3/2010 | Beaurain et al. | |
| 7,695,516 B2 | 4/2010 | Zeegers | |
| 7,695,518 B2 | 4/2010 | Gau | |
| 7,842,088 B2 | 11/2010 | Rashbaum et al. | |
| 7,867,278 B2 | 1/2011 | Lambrecht et al. | |
| 8,002,835 B2 | 8/2011 | Zeegers | |
| 8,021,425 B2 | 9/2011 | Lambrecht et al. | |
| 8,025,697 B2 | 9/2011 | Abdelgany | |
| 8,034,109 B2 | 10/2011 | Zwirkoski | |
| 8,147,556 B2 | 4/2012 | Louis et al. | |
| 8,162,988 B2 | 4/2012 | Delecrin et al. | |
| 8,221,422 B2 | 7/2012 | Mangione | |
| 8,221,457 B2 | 7/2012 | Delecrin et al. | |
| 8,241,359 B2 | 8/2012 | Davis et al. | |
| 8,257,437 B2 | 9/2012 | Lambrecht et al. | |
| 8,257,439 B2 | 9/2012 | Zeegers | |
| 8,262,700 B2 | 9/2012 | Cho et al. | |
| 8,267,999 B2 | 9/2012 | Beaurain et al. | |
| 8,343,219 B2 | 1/2013 | Allain et al. | |
| 8,409,284 B2 | 4/2013 | Lambrecht et al. | |
| 8,409,288 B2 | 4/2013 | Davis et al. | |
| 8,430,915 B2 | 4/2013 | Beaurain et al. | |
| 8,439,931 B2 | 5/2013 | Dinville | |
| 8,454,617 B2 * | 6/2013 | Schaller et al. | 606/90 |
| 8,465,546 B2 | 6/2013 | Jodaitis et al. | |
| 2002/0151979 A1 | 10/2002 | Lambrecht et al. | |
| 2003/0023311 A1 | 1/2003 | Trieu | |
| 2003/0069639 A1 | 4/2003 | Sander et al. | |
| 2004/0030392 A1 | 2/2004 | Lambrecht et al. | |
| 2004/0034429 A1 | 2/2004 | Lambrecht et al. | |
| 2004/0249464 A1 | 12/2004 | Bindseil et al. | |
| 2004/0260397 A1 | 12/2004 | Lambrecht et al. | |
| 2005/0043801 A1 * | 2/2005 | Trieu et al. | 623/17.16 |
| 2006/0052872 A1 * | 3/2006 | Studer et al. | 623/17.13 |
| 2006/0064172 A1 | 3/2006 | Trieu | |
| 2006/0074489 A1 | 4/2006 | Bryan | |
| 2006/0142858 A1 | 6/2006 | Colleran et al. | |
| 2006/0189999 A1 * | 8/2006 | Zwirkoski | 606/90 |
| 2006/0190083 A1 * | 8/2006 | Arnin et al. | 623/17.13 |
| 2006/0217812 A1 | 9/2006 | Lambrecht et al. | |
| 2006/0265077 A1 * | 11/2006 | Zwirkoski | 623/17.16 |
| 2007/0050036 A1 | 3/2007 | Felt et al. | |
| 2008/0125865 A1 * | 5/2008 | Abdelgany | 623/17.16 |
| 2008/0133012 A1 * | 6/2008 | McGuckin | 623/17.12 |
| 2008/0208255 A1 * | 8/2008 | Siegal | 606/246 |
| 2008/0215154 A1 | 9/2008 | Lambrecht et al. | |
| 2008/0221687 A1 * | 9/2008 | Viker | 623/17.16 |
| 2009/0012616 A1 * | 1/2009 | James et al. | 623/17.11 |
| 2009/0281517 A1 | 11/2009 | Lambrecht et al. | |
| 2011/0106264 A1 | 5/2011 | Lambrecht et al. | |
| 2011/0118844 A1 | 5/2011 | Lambrecht | |

FOREIGN PATENT DOCUMENTS

| | | |
|---|---|---|
| DE | 19527975 | 4/1997 |
| DE | 19710392 | 7/1999 |
| DE | 19710392 C1 * | 7/1999 |
| EP | 0577179 | 1/1994 |
| EP | 0621020 | 10/1994 |
| EP | 1157676 | 11/2001 |
| FR | 2797179 | 2/2001 |
| FR | 2838956 | 10/2003 |
| FR | 2913331 | 9/2008 |
| FR | 2917287 | 12/2008 |
| WO | WO9900074 | 1/1999 |
| WO | WO0061037 | 10/2000 |
| WO | WO0062719 | 10/2000 |
| WO | WO0108612 | 2/2001 |
| WO | WO0180786 | 11/2001 |
| WO | WO0217824 | 3/2002 |
| WO | WO02054978 | 7/2002 |
| WO | WO02071921 | 9/2002 |
| WO | WO03007853 | 1/2003 |
| WO | WO03084444 | 10/2003 |
| WO | WO2004100841 | 11/2004 |
| WO | WO2005002474 | 1/2005 |
| WO | WO2005092248 | 10/2005 |
| WO | WO2005122956 | 12/2005 |
| WO | WO2006066228 | 6/2006 |
| WO | WO2006072941 | 7/2006 |
| WO | WO2006091744 | 8/2006 |
| WO | WO2006092015 | 9/2006 |
| WO | WO2008152501 | 12/2008 |

OTHER PUBLICATIONS

Osseous anchoring implant with a polyaxial head and method for installing the implant, U.S. Appl. No. 10/570,080, filed Jun. 9, 2006.

Intervertebral Disc Prosthesis, U.S. Appl. No. 11/051,710, filed Feb. 4, 2005.

Intervertebral Disc Prosthesis and Instrumentation for Insertion of the Prosthesis Between the Vertebrae, U.S. Appl. No. 11/362,253, filed Feb. 24, 2006.

Intersomatic cage with unified grafts, U.S. Appl. No. 11/767,386, filed Jun. 22, 2007.

Modular intervertebral prosthesis, U.S. Appl. No. 11/874,144, filed Oct. 17, 2007.

Vertebral Support Device, U.S. Appl. No. 11/958,285, filed Dec. 17, 2007.

Intervertebral disc prosthesis, surgical methods, and fitting tools, U.S. Appl. No. 12/025,677, filed Feb. 4, 2008.

Intervertebral disc prosthesis insertion assemblies, U.S. Appl. No. 12/527,373, filed Aug. 14, 2009.

Intervertebral Disc Prosthesis, U.S. Appl. No. 12/955,898, filed Nov. 29, 2010.

Instruments and Methods for Removing Fixation Devices from Intervertebral Implants, U.S. Appl. No. 13/158,761, filed Jun. 13, 2011.

Intervertebral Disc Prosthesis, U.S. Appl. No. 13/215,123, filed Aug. 22, 2011.

Interspinous Implant and Implantation Instrument, U.S. Appl. No. 13/369,650, filed Feb. 9, 2012.

Vertebral Cage Device With Modular Fixation, U.S. Appl. No. 13/438,352, filed Apr. 3, 2012.

Plate for osteosynthesis device and method of preassembling such device, U.S. Appl. No. 13/454,927, filed Apr. 24, 2012.

Anchoring Device and System for an Intervertebral Implant, Intervertebral Implant and Implantation Instrument, U.S. Appl. No. 13/520,041, filed Jun. 29, 2012.

Anchoring Device and System for an Intervertebral Implant, Intervertebral Implant and Implantation Instrument, U.S. Appl. No. 13/538,078, filed Jun. 29, 2012.

(56) References Cited

OTHER PUBLICATIONS

Transforaminal intersomatic cage for an intervertebral fusion graft and an instrument for implanting the cage, U.S. Appl. No. 13/585,063, filed Aug. 14, 2012.
Intervertebral Disc Prosthesis, U.S. Appl. No. 13/603,043, filed Sep. 4, 2012.
Intervertebral Disk Prosthesis, U.S. Appl. No. 13/616,448, filed Sep. 14, 2012.
Intervertebral Disc Prosthesis and Instrumentation for Insertion of the Prosthesis Between the Vertebrae, U.S. Appl. No. 13/620,797, filed Sep. 15, 2012.
Intersomatic cage, intervertebral prosthesis, anchoring device and implantation instruments, U.S. Appl. No. 13/732,244, filed Dec. 31, 2012.
Anchoring device and system for an intervertebral implant, intervertebral implant and implantation instrument, U.S. Appl. No. 13/774,547, filed Feb. 22, 2013.
Transforanimal intersomatic cage for an intervertebral fusion graft and an instrument for implanting the cage, U.S. Appl. No. 13/854,808, filed Apr. 1, 2013.
Spinal Osteosynthesis Device and Preparation Method, U.S. Appl. No. 13/873,190, filed Apr. 29, 2013.
Instrumentation and Methods for Inserting an Intervertebral Disc Prosthesis, U.S. Appl. No. 13/892,933, filed May 13, 2013.
Intervertebral disc prosthesis insertion assemblies, U.S. Appl. No. 13/919,704, filed Jun. 17, 2013.
National Institute of Industrial Property (France); Preliminary Search Report in Fench Pub. No. FR2917287; Dec. 19, 2008; National Institute of Industrial Property (France); France; all pages.
World Intellectual Property Organization; Written Opinion of the International Searching Authority for PCT Pub'n No. WO200815250; Dec. 22, 2008; WIPO; Geneva, Switzerland; all pages.
World Intellectual Property Organization; International Preliminary Report on Patentability for PCT Pub'n No. WO2008152501; Jun. 30, 2009; WIPO; Geneva, Switzerland; all pages.
World Intellectual Property Organization; International Search Report for PCT Pub'n WO2008152501; Dec. 22, 2008; WIPO; Geneva, Switzerland; all pages.
European Patent Office, Office Action for Pub'n No. EP2170226; May 6, 2013; EPO; Munich, Germany; all pages.
LDR Medical, by its attorneys; Reply to Office Action for Pub'n No. EP2170226; Jul. 27, 2012; EPO; Munich, Germany; all pages.
European Patent Office; Office Action for Pub'n No. EP2170226; Jan. 17, 2012; EPO; Munich, Germany; all pages.
LDR Medical, by its attorneys; Claim Amendments for Pub'n No. EP2170226; Feb. 10, 2010; EPO; Munich, Germany; all pages.
U.S. Patent & Trademark Office; Issue Notification in U.S. Appl. No. 11/390,711; Mar. 24, 2010; USPTO; Alexandria, Virgina; All Pages.
U.S. Patent & Trademark Office; Notice of Allowance in U.S. Appl. No. 11/390,711; Dec. 3, 2009; USPTO; Alexandria, Virgina; All Pages.
LDR Medical, by its attorneys; Inteview Summary in U.S. Appl. No. 11/390,711; Oct. 28, 2009; USPTO; Alexandria, Virgina; All Pages.
U.S. Patent & Trademark Office; Examiner Interview Summary in U.S. Appl. No. 11/390,711; Sep. 28, 2009; USPTO; Alexandria, Virgina; All Pages.
LDR Medical, by its attorneys; Request for Continued Examination with Reply to Office Action in U.S. Appl. No. 11/390,711; Sep. 23, 2009; USPTO; Alexandria, Virgina; All Pages.
LDR Medical, by its attorneys; Terminal Disclaimer in U.S. Appl. No. 11/390,711; Sep. 23, 2009; USPTO; Alexandria, Virgina; All Pages.
U.S. Patent & Trademark Office; Office Action in U.S. Appl. No. 11/390,711; Mar. 24, 2009; USPTO; Alexandria, Virgina; All Pages.
LDR Medical, by its attorneys; Reply to Office Action in U.S. Appl. No. 11/390,711; Dec. 19, 2008; USPTO; Alexandria, Virginia; All Pages.
U.S. Patent & Trademark Office; Office Action in U.S. Appl. No. 11/390,711; Jun. 19, 2008; USPTO; Alexandria, Virginia; All Pages.
LDR Medical, by its attorneys; Amendment after Notice of Allowance in U.S. Appl. No. 10/060,862; Nov. 3, 2005; USPTO; Alexandria, Virginia; All Pages.
U.S. Patent & Trademark Office; Notice of Allowance in U.S. Appl. No. 10/060,862; Aug. 30, 2005; USPTO; Alexandria, Virginia; All Pages.
LDR Medical, by its attorneys; Reply to Office Action in U.S. Appl. No. 10/060,862; Jun. 22, 2005; USPTO; Alexandria, Virginia; All Pages.
U.S. Patent & Trademark Office; Office Action in U.S. Appl. No. 10/060,862; Feb. 18, 2005; USPTO; Alexandria, Virginia; All Pages.
LDR Medical, by its attorneys; Request for Continued Examination with Reply to Office Action in U.S. Appl. No. 10/060,862; Dec. 8, 2004; USPTO; Alexandria, Virginia; All Pages.
U.S. Patent & Trademark Office; Office Action in U.S. Appl. No. 10/060,862; Nov. 22, 2004; USPTO; Alexandria, Virgina; All Pages.
LDR Medical, by its attorneys; Reply to Office Action in U.S. Appl. No. 10/060,862; Nov. 8, 2004; USPTO; Alexandria, Virgina; All Pages.
U.S. Patent & Trademark Office; Office Action in U.S. Appl. No. 10/060,862; Jun. 8, 2004; USPTO; Alexandria, Virgina; All Pages.
LDR Medical, by its attorneys; Reply to Office Action in U.S. Appl. No. 10/060,862; Mar. 19, 2004; USPTO; Alexandria, Virgina; All Pages.
LDR Medical, by its attorneys; Reply to Office Action in U.S. Appl. No. 10/060,862; Feb. 9, 2004; USPTO; Alexandria, Virginia; All Pages.
U.S. Patent & Trademark Office; Office Action in U.S. Appl. No. 10/060,862; Aug. 8, 2003; USPTO; Alexandria, Virgina; All Pages.

* cited by examiner

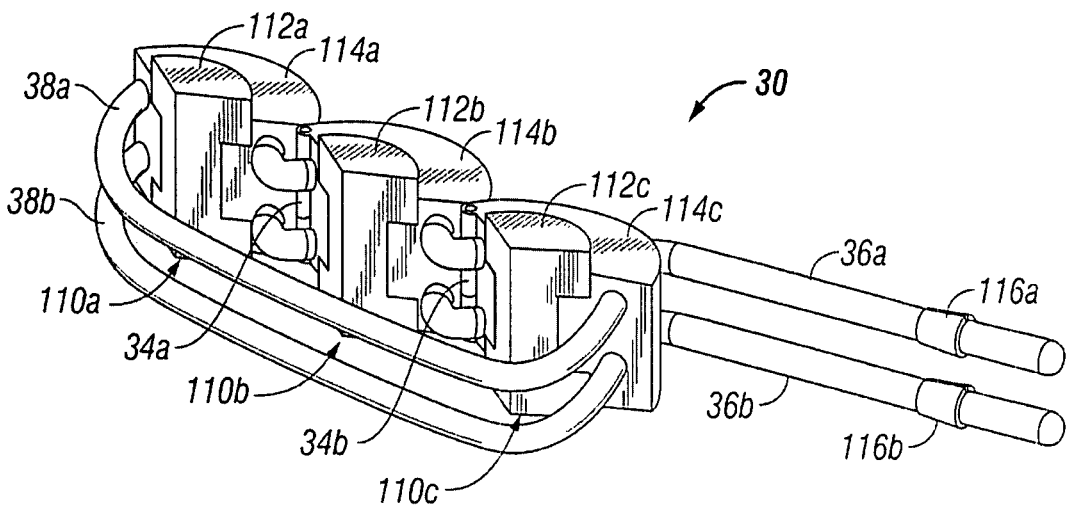
*FIG. 13A*
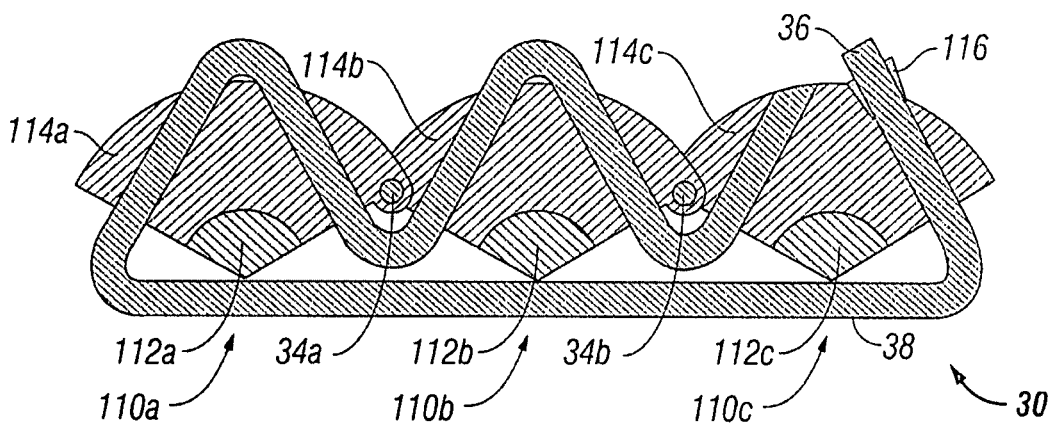
*FIG. 13B*
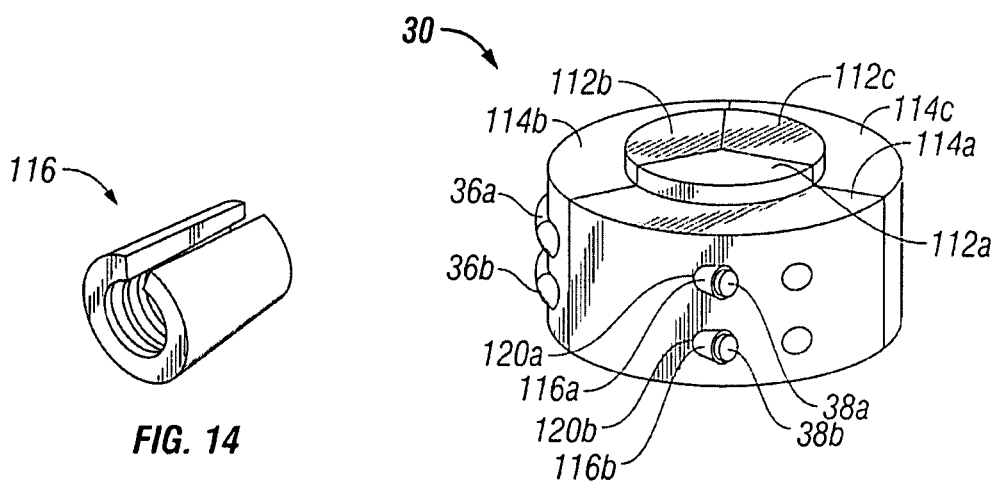
*FIG. 14*
*FIG. 15*

NUCLEUS PROSTHESES

RELATED APPLICATIONS

This application claims priority under 35 U.S.C. §119 to French Patent Application No. 07 04326, filed in FRANCE on Jun. 15, 2007.

TECHNICAL FIELD

This disclosure relates to nucleus prostheses for implantation in an intervertebral disc or in an intervertebral disc space, and more particularly to replace a nucleus pulposus of an intervertebral disc.

BACKGROUND

An intervertebral disc located between two vertebrae in the spine provides structural support and distributes forces exerted on the spinal column. Besides holding the vertebrae together, enabling upright posture and natural curvature of the spine (lordosis or kyphosis, for example, within normal physiological ranges), a healthy intervertebral disc enables flexion, extension, lateral bending, and axial rotation of the vertebrae.

The major components of an intervertebral disc include the annulus fibrosus, the nucleus pulposus, and cartilage endplates. The annulus fibrosus is a tough, fibrous ring attached to the vertebrae directly above and below the disc space. The tire-like annulus fibrosus supports the adjacent vertebrae and limits their relative displacements in translation and rotation. The annulus fibrosus also contains the nucleus pulposus. The nucleus pulposus is the central portion of the disc, comprising a relatively soft, gel-like substance that provides many of the articulation and cushioning properties of the intervertebral disc.

Intervertebral discs may be injured or become damaged by disease or aging. A common problem is disc herniation, in which portions of the nucleus pulposus is extruded through an opening in the annulus. Portions of the nucleus pulposus protruding into the vertebral canal may press on a spinal nerve, often resulting in nerve damage, intense pain, numbness, reduced mobility, and muscle weakness. When degeneration or disease of the natural intervertebral disc has progressed to the point where non-operative care such as medication, injections, and/or physical therapy is ineffective, surgical intervention may be required.

A common procedure for treatment of a degenerated or diseased intervertebral disc involves removal of the natural tissues of the disc and fusion of the adjacent vertebrae (intervertebral arthrodesis). Another frequently used procedure, generally considered before the intervertebral arthrodesis, implies the withdrawal of the natural tissues and the replacement of the intervertebral disc by an intervertebral disc prosthesis.

SUMMARY

Various embodiments of the present invention provide nucleus prostheses comprising a plurality of segments, including a leading segment and a trailing segment, and a linkage coupling the segments. The prosthesis of various embodiments has an open position in which the segments are disposed along the linkage in a serial line with the leading segment at an end of the serial line and the trailing segment at another end of the serial line, and a closed position in which the segments are disposed to form a disc shape with the leading segment and the trailing segment substantially apposed.

Various embodiments of the instant invention are configured for use as a fusion device (e.g., for an arthrodesis). However, fusion eliminates the mobility between the adjacent vertebrae and can transfer stresses and movements to the intervertebral discs above and/or below the point of fusion. Accordingly, a treatment that maintains some mobility of the vertebrae directly above and below the disc space may be preferred. Various embodiments of the present invention may be configured for use to maintain some mobility of the vertebrae directly above and below the disc space.

Various embodiments of a method are disclosed (as an illustration). For example, an embodiment of method includes inserting a plurality of linked segments into an annulus fibrosus and closing the nucleus prosthesis so that a first segment (e.g., a leading segment) inserted into the annulus fibrosus and a last segment (e.g., a trailing segment) inserted into the annulus fibrosus are substantially abutted.

The details of one or more embodiments of the invention are set forth in the accompanying drawings and the descriptions of this disclosure. Other features, objects, and advantages of the invention will be apparent after appreciating the description, drawings, and the claims.

BRIEF DESCRIPTIONS OF THE DRAWINGS

FIGS. 13A and 13B are a perspective view and a plan view, respectively, of man exemplary nucleus prosthesis in accordance with some embodiments.

FIG. 14 is a perspective view of an exemplary retainer for use with an nucleus prosthesis in accordance with some embodiments.

FIG. 15 is a perspective view of an exemplary nucleus prosthesis in accordance with some embodiments.

Figure 26:
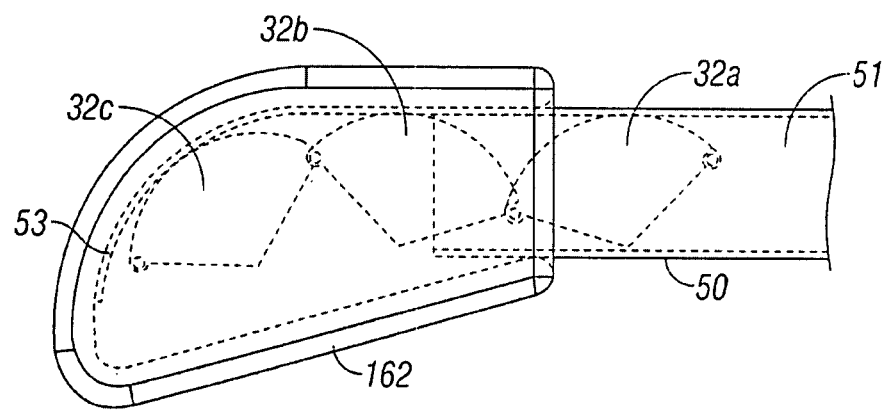

FIG. 26 schematically depicts the insertion of a prosthesis in accordance with some embodiments.

Figure 27:
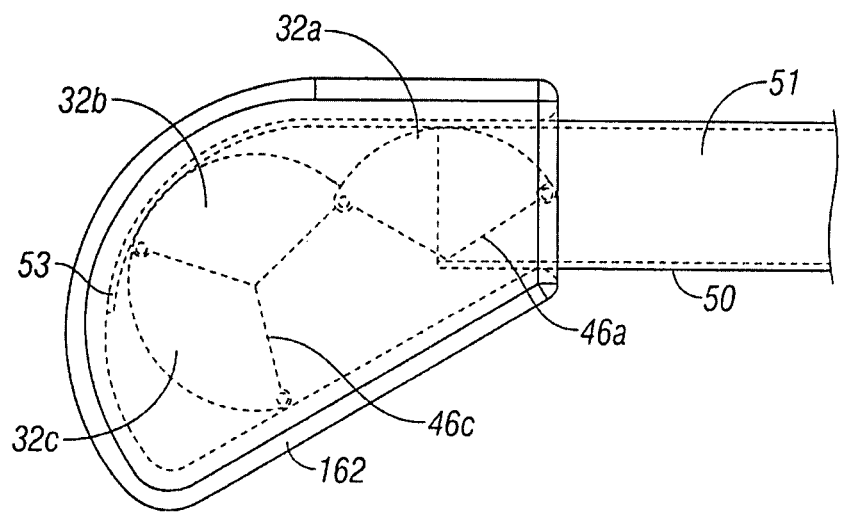

FIG. 27 schematically depicts the insertion of a prosthesis in accordance with some embodiments.

Figure 28:
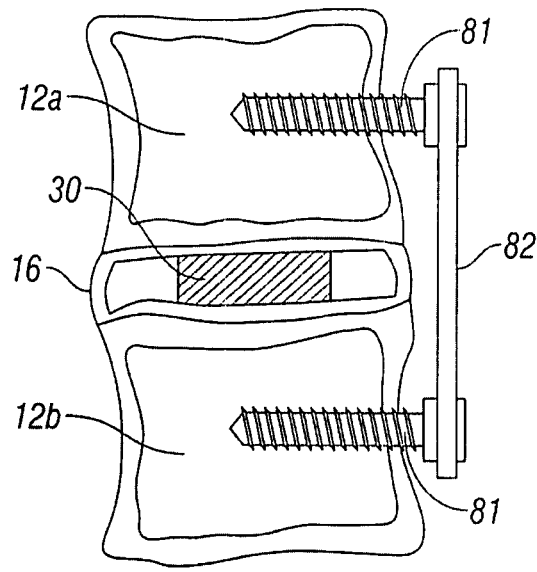

FIG. 28 depicts an embodiment comprising spinal fixation components.

Figure 29:
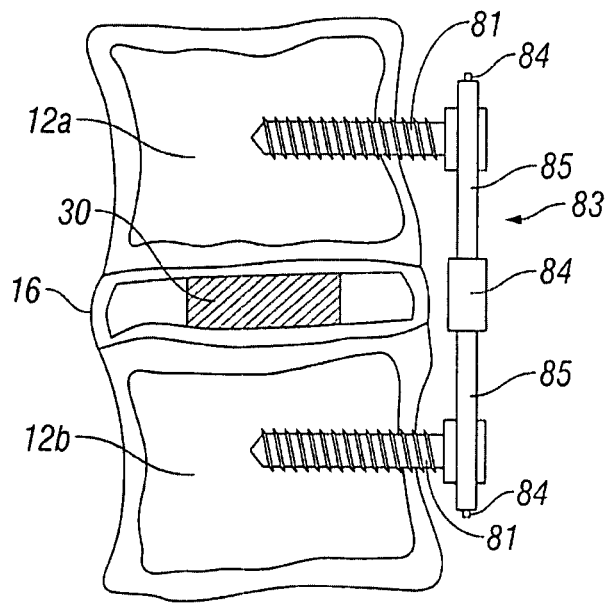

FIG. 29 depicts an embodiment comprising flexible spinal stabilization components.

Figure 30:
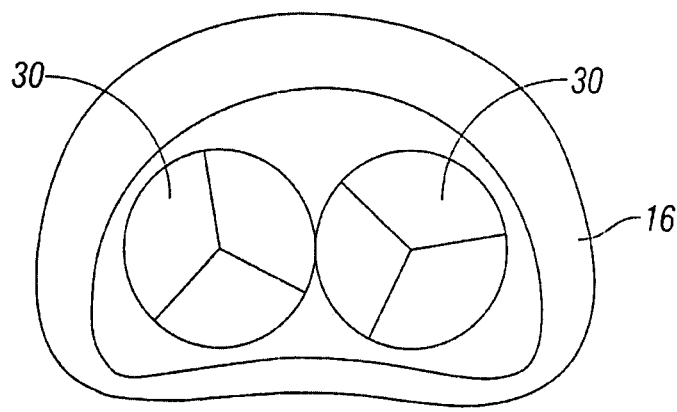

FIG. 30 depicts an embodiment comprising multiple prostheses.

Figure 31:
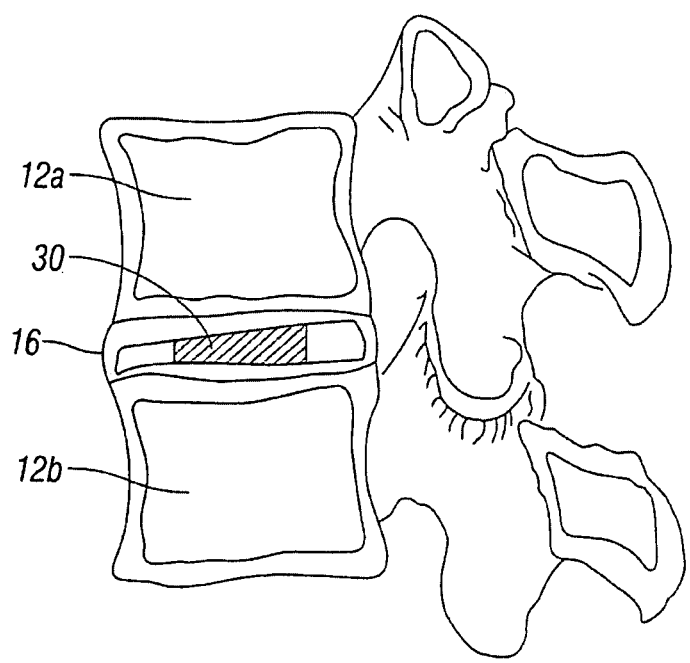

FIG. 31 depicts an embodiment configured to mitigate or impose lordosis.

DETAILED DESCRIPTION OF VARIOUS EMBODIMENTS

Figure 1:
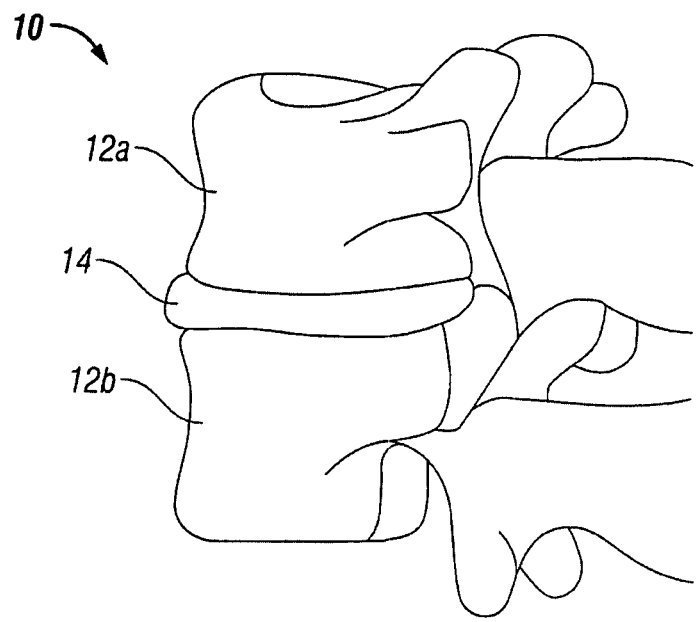
FIG. 1 is a side view of a section of a spine.
Figure 2:
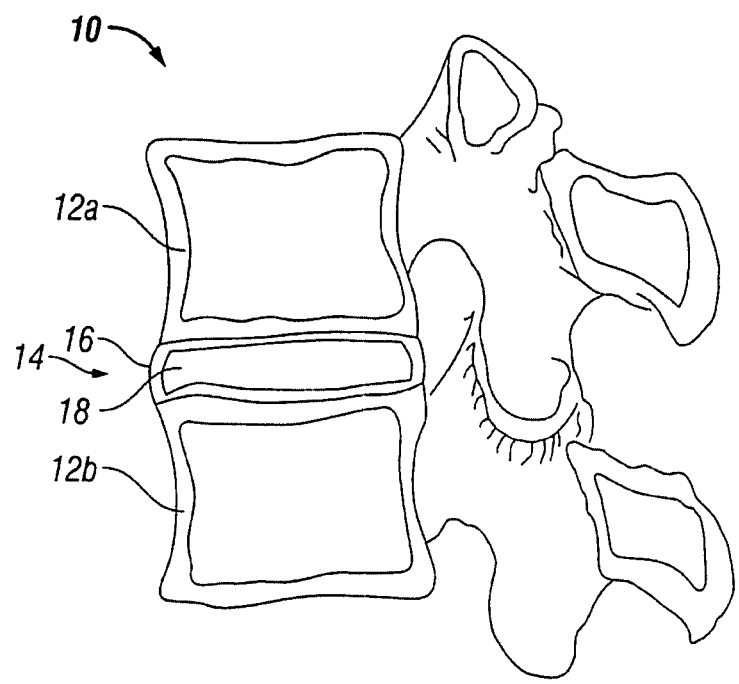
FIG. 2 is a cross-sectional view of a section of a spine.

FIG. 1 is a representative side view of a section 10 of a spine. In particular, the illustrated section 10 shows an intervertebral disc 14 between two vertebrae 12a and 12b. As shown in the cross-sectional view of section 10 depicted in FIG. 2, disc 14 includes annulus fibrosus 16 and nucleus pulposus 18. As described above, if annulus fibrosus 16 ruptures, nucleus pulposus may emerge from the rupture and place pressure on spinal nerves (not illustrated).

Figure 3A:
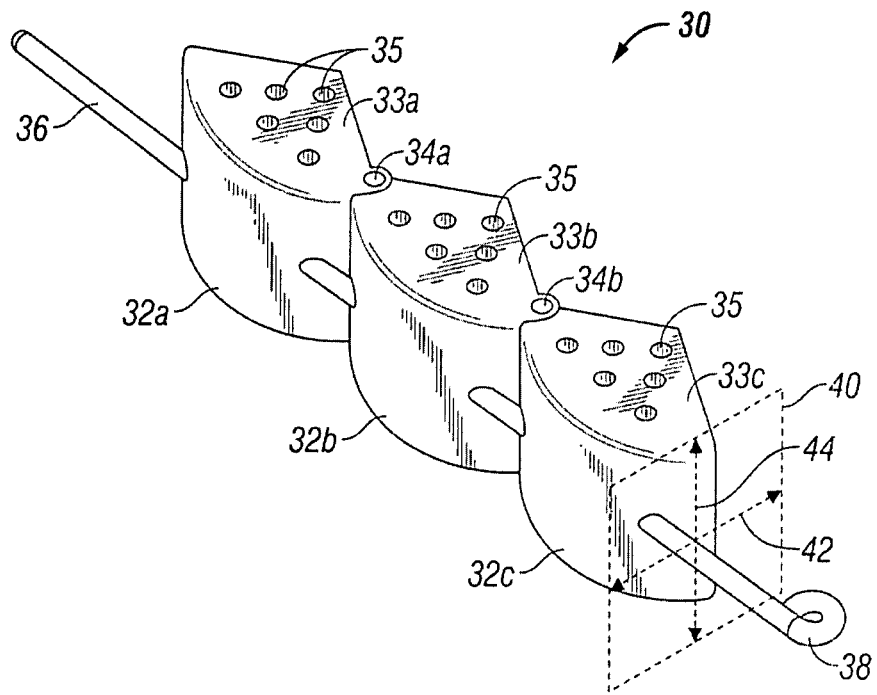
FIGS. 3A and 3B are perspective views of exemplary nucleus prostheses in accordance with some embodiments.
Figure 3B:
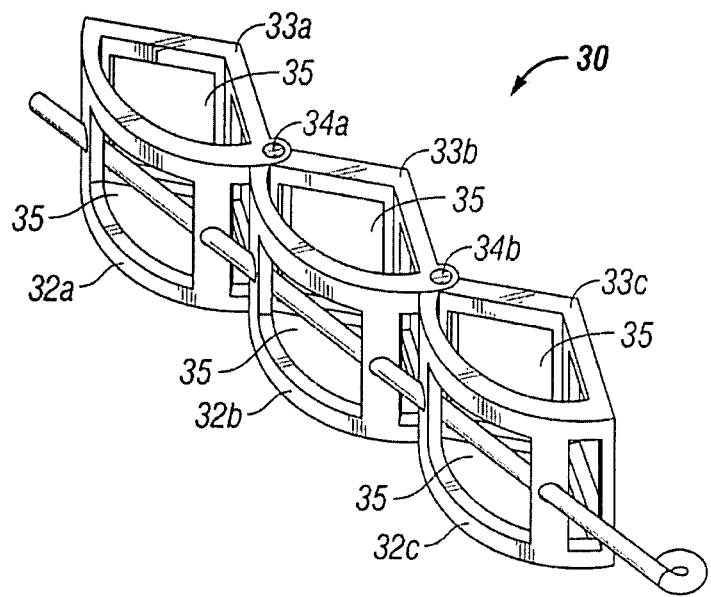

FIGS. 3A and 3B depict exemplary nucleus prostheses 30 in an open position in accordance with various embodiments. In various embodiments, the implantation may be arranged to alleviate the discomfort caused by a herniated disc (or other degenerative or pathological condition) while still providing a degree of mobility for the vertebrae. The prosthesis 30 can be surgically implanted within the annulus fibrosus 16, for example if the annulus fibrosus 16 remains sufficiently healthy and intact. In some embodiments, the prosthesis 30 can be employed to augment the remaining nucleus pulposus 18. Various embodiments of the prosthesis 30 can be employed to replace a nucleus pulposus 18 that has been completely extracted. The prosthesis 30 can also be devised for insertion and deployment in an intervertebral disc space that has undergone a complete discectomy (complete removal of the intervertebral disc). However, in this case, the prosthesis would be used as a fusion intersomatic cage and may comprise apertures or voids (or windows or recesses) as explained below. This embodiment of the prosthesis as a fusion cage may also comprise osseous anchoring means, for example of known type, for fixing the prosthesis on the adjacent vertebrae before the fusion is complete. Prosthesis 30 may also be employed to relieve back conditions other than a herniated disc; for example, the prosthesis 30 can be used to alleviate problems related to a hardening of annulus fibrosus 16 and/or dehydration of the nucleus pulposus, or other degenerative or pathological conditions.

In various embodiments in which the prosthesis 30 is used as a fusion device, it can be deployed within remaining portions of the annulus fibrosus or deployed within the intervertebral disc space following a complete discectomy. As a fusion device, the prosthesis 30 can be configured to promote ingrowth of osseous tissue and can be disposed in the disc space to facilitate fusion of the vertebrae 12a and 12b.

Prosthesis 30 includes a plurality of segments 32. FIGS. 3A and 3B each respectively illustrates three segments 32a, 32b, and 32c, but in alternate embodiments, prosthesis 30 may include any suitable number of segments from two on up. For example, prosthesis 30 may have two segments, four segments, five segments, six segments, and so on. Segments 32 may be formed out of a rigid or semi-rigid material suitable for maintaining the spacing between the vertebrae 12a and 12b. For example, segments 32 may be formed out of a semi-rigid plastic material that is at least partially elastic to enable segments 32 to better absorb stresses placed on the segments after prosthesis 30 has been implanted into the annulus fibrosus 16. In other embodiments, segments 32 may also be rigid in some or all portions of the segments 32. Combinations of rigid and semi-rigid portions may be used in various embodiments of segments 32 to provide desired support properties.

Segments 32 may be linked together by at least one link. For example in FIGS. 3A and 3B, segments 32 are linked by hinge 34a (between segments 32a and 32b) and hinge 24b (between segments 32b and 32c). Segments 32 may also be linked together by one or more other linking elements like a flexible link, for example such as a ligament 36. The ligament 36 may take a secant path through one or more of the segments 32, through a passage passing through the segment(s) or through a path following grooves along the segments. In other configurations, the ligament 36 may take other suitable paths (e.g., radial, annular, arcuate, incurvate, ascending, descending, weaving, etc.) through segments 32. Ligament 36 may be composed of synthetic fibers, such as Dacron® polyester fiber produced by E.I. du Pont de Nemours and Company of Wilmington, Del., other polymers or plastics, or other suitable materials. Other types of linkages may also be used to couple segments 32, for example is discussed further below.

Ligament 36 may also include a closure element, for example such as loop 38. Loop 38 can be used during the surgical implantation of the prosthesis 30, as described below. Other fastening or retaining devices may be employed as a closure element in place of a loop, such as for example a hook, catch, or clamp. In an open position of prosthesis 30, segments 32 may be disposed along ligament 36 in a serial line (i.e., one after another) from segment 32c closest to loop 38 to segment 32a furthest from loop 38. In an open position, the prosthesis 30 will have a leading segment, such as for example segment 32c, and a trailing segment, such as for example segment 32a, with the designations "leading" and "trailing" established by the direction in which prosthesis 30 is implanted (see, e.g., FIGS. 6, 25). As such, in an open position, prosthesis 30 has a cross-sectional area 40 generally bounded in width by the width 42 of the segments 32 and generally bounded in height by a vertical height 44 of the segments 32. Prosthesis 30 may have any suitable height 44 or width 42. For example, the height 44 and width 42 of segments 32 can be selected based on a height and width of a patient's intervertebral disc 14 or the intervertebral disc space.

Segments 32 are shaped such that when the prosthesis 30 is in a closed position (see FIGS. 4A, 4B, 7, 10, and 12 showing almost closed positions, and FIGS. 15 and 30 showing closed positions), segments 32 form a shape suitable for supporting the vertebrae 12a and 12b. Suitable shapes may vary depending on the anatomy of the patient and on the intended deployment of the prosthesis 30, for example deployment within the annulus fibrosus, deployment in an intervertebral disc space that has undergone a complete discectomy, deployment as a fusion device, or deployment to correct or impose a lordosis or kyphosis condition. Regardless of the intended deployment, the suitable shapes for supporting the vertebrae 12a and 12b will be referred to in this document as a "disc shape." This designation concerns the shape of the nucleus with respect to the intervertebral disc. For the purposes of this document, a disc shape may be in the form of a straight and flat cylinder as shown on the figures. However, other shapes may be used, for example a generalized cylinder, i.e., a shape defined by sweeping a variable cross-section along an axis such as a line or a more general space curve, bounded on both sides by surfaces that may be flat, convex, concave, or a combination of the foregoing. Indeed, a straight cylinder is defined by a circular base and a straight height, but a generalized cylinder may be defined by a base of any curved or polygonal shape and a curved or straight height. The instant nucleus prosthesis may have any shape of these types of generalized cylinder. The vertebral contact surfaces of the generalized cylindrical shapes may have edges taking any suitable shape (e.g., a circle, an ellipse, an oval, an oblong, an egg shape, a polygon, etc.). A disc shape alternatively may be in the form of a generalized ellipsoid, a polyhedron, a generalized toroid, or another shape. The disc shape formed by segments 32 when the prosthesis 30 is in a closed position may be solid or may be generally hollow. In the embodiments illustrated in FIGS. 3A and 3B, segments 32 each have a wedge, pie, or tapered shape, but other shapes may be used.

Figure 4A:
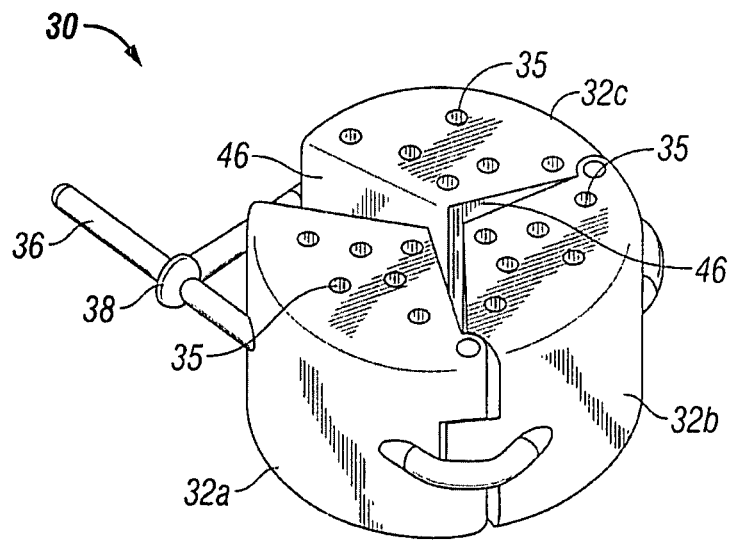
FIGS. 4A and 4B are top views of exemplary nucleus prostheses in accordance with some embodiments.
Figure 4B:
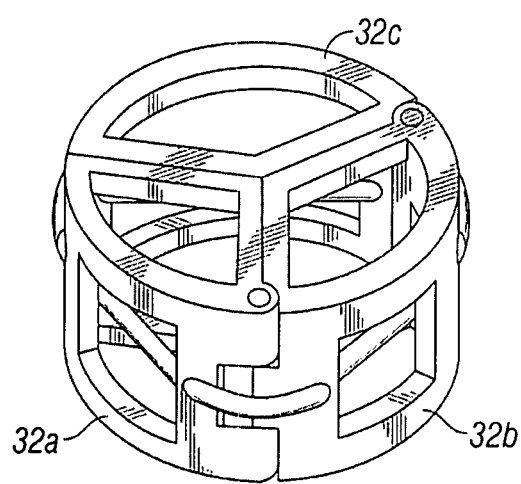

Various embodiments may be feature chamfered, tapered, or beveled edges to mitigate damage to the vertebral surfaces. For example, the embodiments illustrated in FIGS. 3A and 4A have chamfered edges between the sidewalls and the upper and lower surfaces of the segments. In addition, in some embodiments the internal face 46 of the leading segment may have upper, lower, and/or outer edges that are chamfered, for example as illustrated in FIGS. 3A and 4A, to facilitate closing of the prosthesis 30 and mitigate damage to surrounding tissue during the closing.

The disc shape formed by segments 32 when the prosthesis 30 is in a closed position may have one or more apertures or voids along either or both of its vertebral contact surfaces and/or along one or more external and/or internal walls or faces of one or more of the segments of the prosthesis. These apertures may consist in blind holes or holes passing through the segments. FIG. 3A, for example, depicts an embodiment in which apertures or voids 35 are disposed along the vertebral contact surfaces 33a, 33b, and 33c. In this embodiment, the apertures or voids 35 are relatively small cylindrical holes. The voids 35 can be devised to accommodate bone ingrowth from the adjacent vertebra, which may promote stability of the prosthesis 30 within the annulus fibrosus 16 or within the intervertebral disc space. Apertures or voids can also be configured to promote fusion. For example, FIG. 3B depicts an embodiment of a prosthesis 30 having numerous apertures 35 configured for bone ingrowth to promote fusion of the vertebrae 12a and 12b. The apertures 35 on the upper and lower surfaces of the segments may be connected, so that bone ingrowth can extend continuously from the upper vertebra to the lower vertebra. In addition, the apertures can connect along the internal faces of the segments to promote contiguous bone ingrowth throughout the prosthesis 30. For example, the embodiment of the prosthesis 30 shown in FIG. 3B is substantially hollow, but other embodiments may employ different configurations and extents of the apertures or voids. Bone ingrowth for the embodiments of FIGS. 3A and 3B, as well as other embodiments, can be promoted using osseous tissue or natural or synthetic substitutes for osseous tissue, or by other techniques.

FIG. 4 depicts prosthesis 30 in an almost closed position in accordance with various embodiments. When closed, segments 32a, 32b, and 32c of such embodiments will have a disc shape generally in the form of a cylinder. In particular, in a closed position of prosthesis 30, the segments 32 fold around the hinges 34a and 34b such that a face 46 of a segment 32 is substantially juxtaposed to a face 46 of an adjacent segment 32. When the prosthesis 30 is in a closed position, a face 46 of segment 32a is adjacent to a face 46 of segment 32c. In other words, when the prosthesis 30 is in a closed position, the first segment in the series of segments 32 is generally adjacent to the last segment in the series.

Figure 5:
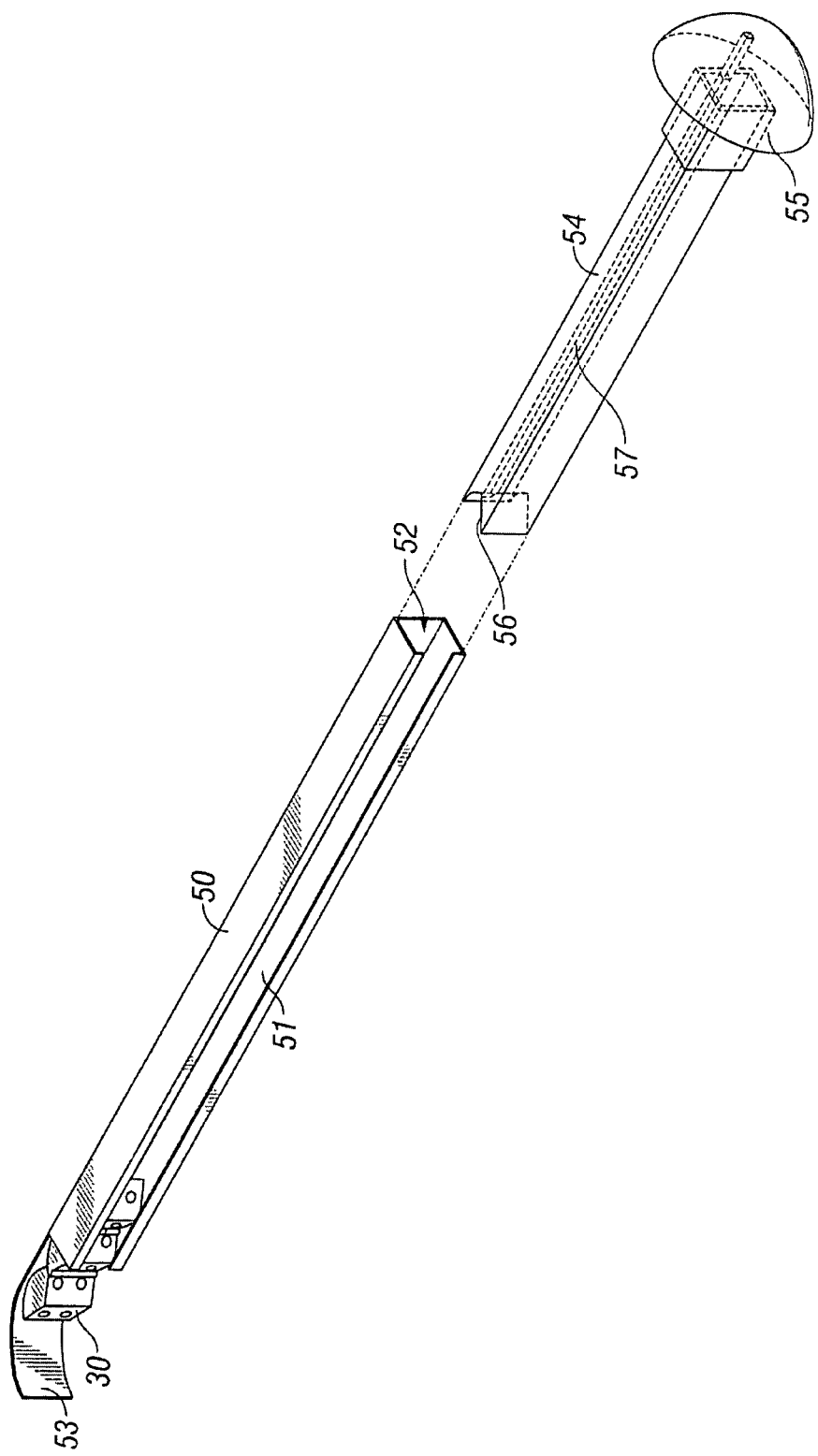
FIG. 5 is a perspective view of an insertion instrument in accordance with some embodiments.

FIG. 5 depicts an insertion instrument in accordance with various embodiments. In the illustrated embodiment, the insertion instrument is a guide configured as a chute 50 having a channel 51 extending along the length of the chute 50. The insertion instrument has an open end 52 configured to receive a prosthesis, such as, for example, a hinged prosthesis 30 as illustrated. The channel 51 preferably has an internal cross section complementary to the cross-sectional profile 40 of the prosthesis (i.e., complementary to the transversal section of the prosthesis in an open position). In some embodiments, an internal cross section of the insertion instrument complementary to the cross-sectional profile 40 of the prosthesis will tend to keep the segments of the prosthesis, such as segments 32a, 32b, and 32c of the illustrated prosthesis 30, in good alignment while the prosthesis traverses the channel to reach the insertion point (i.e., within the annulus fibrosus or within the intervertebral disc space in the case of a complete discectomy). A diverter, such as the curved deflector 53, optionally may be disposed at the end of insertion instrument 50. The diverter may have a flexibility adapted to facilitate closure of prosthesis segments while still facilitating withdrawal of the insertion instrument.

Optionally, the diverter may have selectable flexibility, for example by having setting for insertion of the prosthesis in which the diverter is relatively rigid while having another setting for withdrawal of the insertion instrument in which the diverter is relatively flexible. For example, the deflector may have multiple articulated segments along the insertion direction through which a common conduit passes. During insertion of the prosthesis, for example, a "J" shaped spring steel spline (having memory shape or spring properties) having an end with an appropriate curvature may be forced into a straight position and passed along the length of the insertion tool through a conduit into the conduit of the deflector segments. When the spline is fully inserted through the insertion tool conduit and the common conduit through the articulated deflecting segments, the deflector would tend to maintain the appropriate curvature for insertion of the prosthesis. When the prosthesis has been inserted, the spline could be withdrawn fully from the conduits, releasing conformal forces on the articulated deflecting segments and allowing them to articulate and align with each other during withdrawal of the insertion instrument.

In various embodiments, a positioner may be used during insertion of the prosthesis. For example, the positioner depicted in FIG. 5 is configured as a rod 54. The positioner may be configured with a control, for example such as the handle or knob 55 of the embodiment illustrated in FIG. 5. The positioner may have a coupler, for example such as the notch 56 illustrated in FIG. 5. In the illustrated embodiment, the notch 56 has a surface-complementary to the trailing end of a prosthesis segment, but other coupling means may be used. The positioner may also have a transit for a linking element or a part thereof. For example, the embodiment illustrated in FIG. 5 has a transit configured as a channel 57, through which an end portion of a ligament 36 can extend.

In various embodiments, a positioner may be used to urge a prosthesis along an insertion instrument. In some embodiments, the positioner may be used to maintain the nucleus prosthesis within the annulus fibrosus 16 or within the intervertebral disc space while a linking element, such as ligament 36, is employed to close the prosthesis, and may also be used to further urge the prosthesis into proper position during the closure operation.

Figure 6:
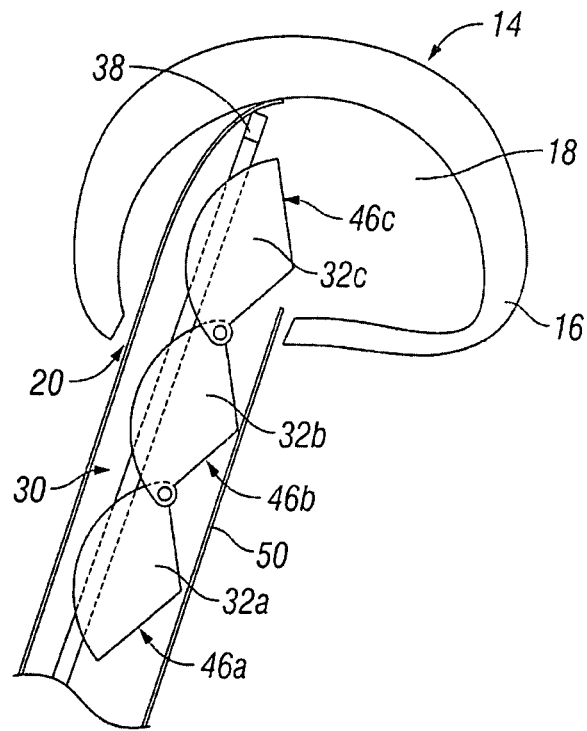
FIG. 6 is an obverse cross-sectional view of an exemplary nucleus prosthesis being surgically implanted into an intervertebral disc in accordance with some embodiments.

FIG. 6 illustrates a technique that may be used to surgically implant a nucleus prosthesis 30 into an annulus fibrosus 16 in accordance with various embodiments. As shown, an insertion instrument, for example such as a chute or tube 50, may be inserted through a surgical incision 20 in the annulus fibrosus 16 into the site of the nucleus pulposus 18. Some or all of nucleus pulposus 18 may be removed, through chute 50 (removal not shown) or otherwise. At that point, prosthesis 30, in an open position, is fed through chute 50 into the annulus fibrosus 16 with loop 38 entering first. The cross-sectional area of the surgical incision may be generally the same as the cross-sectional profile 40 even though, as described below, prosthesis 30 in a closed position has a cross-sectional area larger than the profile 40.

Figure 7:
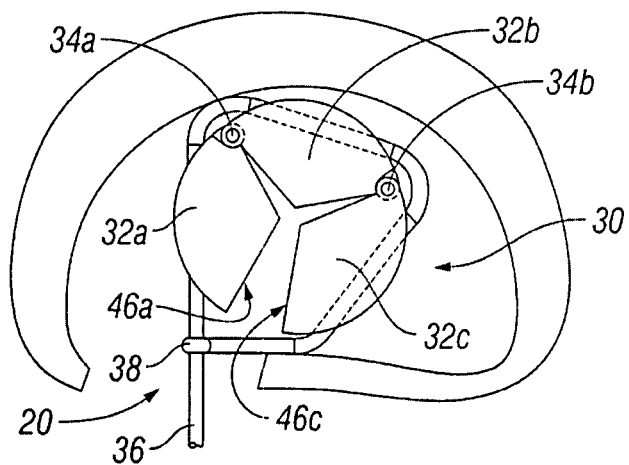
FIG. 7 is an obverse cross-sectional view of an exemplary nucleus prosthesis being surgically implanted in accordance with some embodiments.

FIG. 7 illustrates prosthesis 30 in an almost closed position during the surgical implantation of prosthesis 30 within the annulus fibrosus 16 in accordance with various embodiments. When prosthesis 30 is fed into the annulus fibrosus 16, loop 38 and segment 32c make contact with a surface of annulus fibrosus 16 causing segment 32c and segment 32b to fold about hinge 34b. As prosthesis 30 continues into the annulus fibrosus 16, segment 32b and segment 32a will subsequently fold about hinge 34a. At that point, loop 38 can engage the other end of ligament 36 (near segment 32a). Once loop 38 is engaged with the other end of the ligament, prosthesis 30 can be urged into a closed position by pulling on the end of the ligament 36 opposite the loop 38. Engagement of loop 38 with the other end of ligament 36 can be configured to cause ligament 36 to tighten around segments 32a, 32b, and 32c, and to urge the prosthesis 30 into a closed position. The insertion instrument 50 may of course be used here to facilitate the removal of the prosthesis, as detailed below.

This tightening may be aided by one or more lubricants on ligament 36. As mentioned above, when prosthesis 30 is in a closed position, face 46a of segment 32a and face 46c of segment 32c are substantially apposed. A positioner 54 may be used to hold the prosthesis 30 in position while ligament 36 is tightened.

Next, loop 38 can be permanently fastened to maintain prosthesis 30 in a closed position. In alternate embodiments, other techniques can be used to keep prosthesis 30 in a closed position. After prosthesis 30 is in a closed position, ligament 36 can be trimmed, chute 50 can be removed, and annulus fibrosus 16 can be closed. Preferably the surgical incision will be sized so that the prosthesis 30 in a closed position will not fit through the surgical incision, although in some embodiments, prosthesis 30 can be returned to an open position for removal via the surgical incision.

Figure 8:
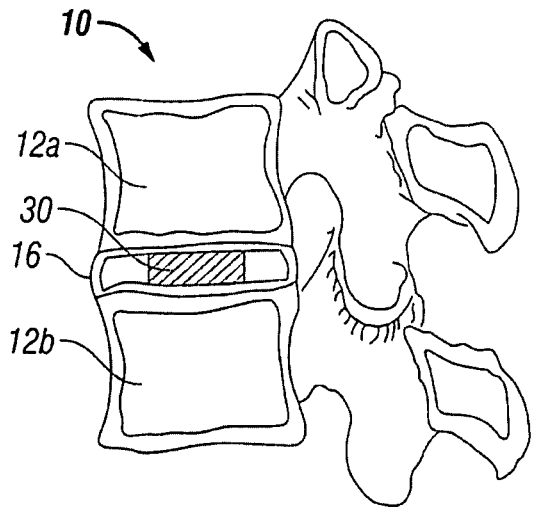
FIG. 8 is a cross-sectional view of a section of the human backbone after the surgical implantation of an exemplary nucleus prosthesis in accordance with some embodiments.

FIG. 8 illustrates the section 10 of the spine after a prosthesis 30 has been surgically implanted into the annulus fibrosus 16. As shown, a prosthesis 30 is placed within annulus fibrosus 16 to facilitate vertebral support and shock absorption. FIG. 8 illustrates a non-fusion installation of a nucleus prosthesis 30 inside annulus librosus 16. However, it will be appreciated that any of the prostheses described herein could alternatively be reconfigured for use as a fusion device within the annulus fibrosus 16 or within the intervertebral disc space that has undergone a complete discectomy.

Figure 9:
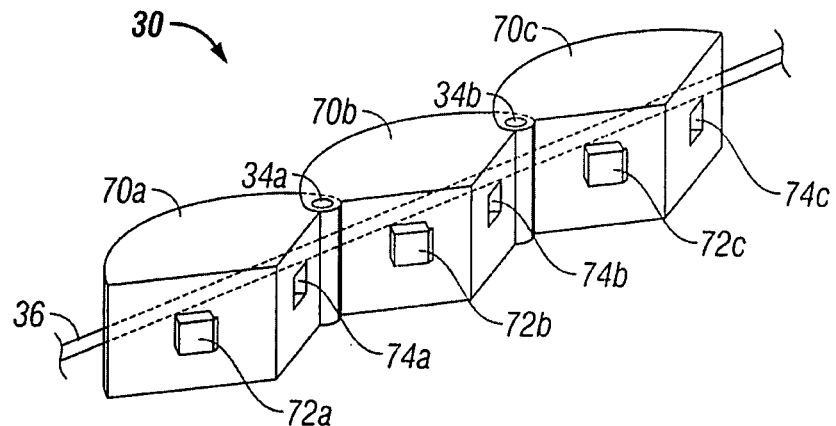
FIG. 9 is a perspective view of an exemplary nucleus prosthesis in accordance with some embodiments.
Figure 10:
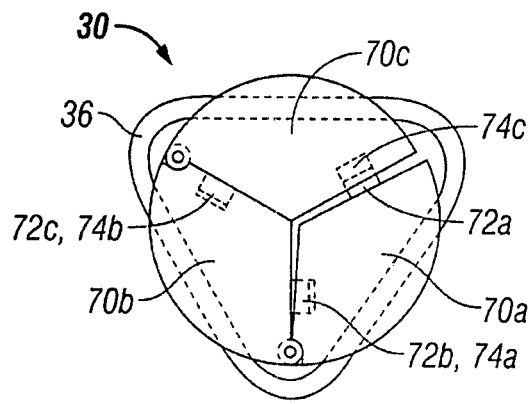
FIG. 10 is a top view of an exemplary nucleus prosthesis in accordance with some embodiments.

FIG. 9 illustrates another embodiment of prosthesis 30. In this embodiment, prosthesis 30 includes segments 70a, 70b, and 70c coupled together via hinges 34a and 34b and ligament 36. In alternate embodiments, other couplings and/or linkages may be used. Segments 70 each include respective male interlocking elements 72 and female interlocking elements 74. As shown in FIG. 10, a top view of this embodiment of prosthesis 30, interlocking elements 72 and 74 interlock with each other when prosthesis 30 is in a closed position. In various embodiments, male interlocking elements 72 are formed out of the same elastic material as segments 70. Interlocking elements 72 and 74 may be configured to prevent both horizontal and vertical movement between individual segments 70 when this embodiment of prosthesis 30 is in a closed position, or may be configured to allow limited relative movements of segments 70 horizontally and/or vertically.

Figure 11:
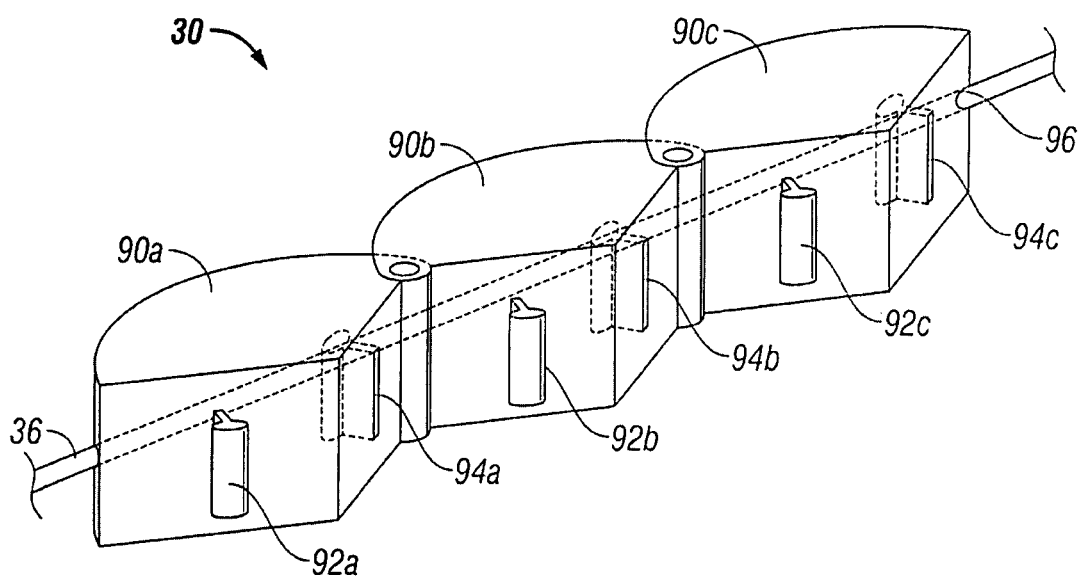
FIG. 11 is a perspective view of an exemplary nucleus prosthesis in accordance with some embodiments.

FIG. 11 illustrates a perspective view of another embodiment of prosthesis 30 in which the individual segments of the prosthesis 30 are able to move vertically with respect to one another when prosthesis 30 is in a closed position. This embodiment of prosthesis 30 includes segments 90a, 90b, and 90c linked together via ligament 36. In this embodiment, the ligament 36 traverses through bores 96 that take a secant path through each segment 90a, 90b, and 90c, and through optional grooves 98 along the edges of the segments. In other embodiments, the grooves 98 could extend around one or more of the segment 90a, 90b, and 90c in lieu of holes 96. Other combinations of bores 96 and/or grooves 98 will be apparent to those of skill in the art after appreciating this disclosure. In still other alternate embodiments, other linkages may also be used to couple segments 90 together.

Figure 12:
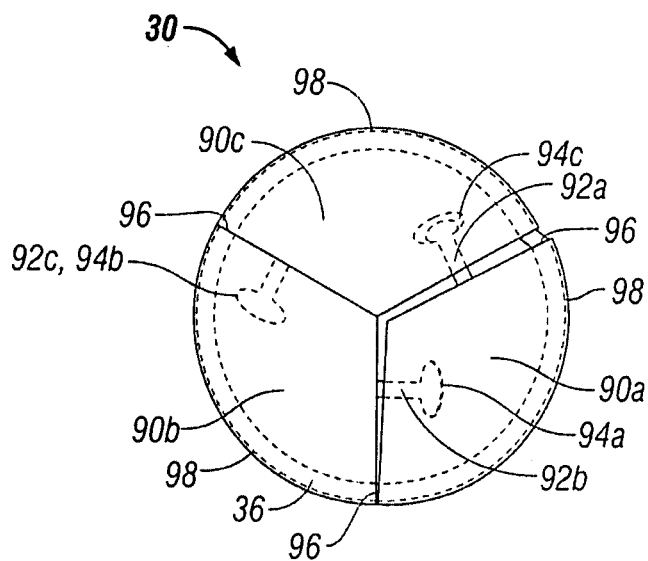
FIG. 12 is a top view of an exemplary nucleus prosthesis in accordance with some embodiments.

In the embodiment shown in FIGS. 11 and 12, the segments 90 each include male interlocking elements 92 and female interlocking elements 94. In this embodiment, female interlocking elements 94 are longer in the vertical direction than the male interlocking elements 92. This feature enables the male interlocking elements 92 to slide within the female interlocking elements 94, permitting vertical movements of segments 90 with respect to one another. In other embodiments, other suitable mechanism may be employed for interlocking segments 90 while providing relative vertical movements of the segments 90.

As shown in FIG. 12, a top view of this embodiment of prosthesis 30, joints are formed by interlocking elements 92 and 94 engaging each other when prosthesis 30 is in a closed position. The male interlocking elements 92 may slide vertically within the female interlocking elements 94. For example, the male interlocking elements 92 may be configured as pins, and the female interlocking elements 94 may be configured as channels have an interior shape complementary to the external shape of the pins. Thus, the interlocking elements 92 and 94 are configured to enable vertical movement between individual segments 90 when embodiments of prosthesis 30 such as this are in a closed position. In various embodiments, the male interlocking elements 92 are formed out of the same elastic material as segments 90.

FIGS. 13A and 13B illustrate another embodiment of prosthesis 30. This embodiment of prosthesis 30 includes segments 110a, 110b, and 110c. Each of the segments 110 includes a first elasticity region 112 and a second elasticity region 114 in which the first and second elasticity regions are composed of materials with different constants of elasticity. In some embodiments, segments 110a, 110b, and 110c may alternatively exhibit an elasticity gradient through portions of segments 110a, 110b, and 110c. Segments having different elasticity regions or an elasticity gradient, of course, similarly may be deployed in various other embodiments.

In this embodiment, segments 110a, 110b, and 110c are linked together with two ligaments 36a and 36b. As with earlier described embodiments, ligaments 36a and 36b are used to urge segments 110 into a closed position, and may be used to maintain the prosthesis 30 in a closed position. In the embodiment depicted in FIGS. 13A and 13B, ligaments 36a and 36b are woven through the segments 110, but other suitable ligament structures can be used (e.g., a single ligament traversing a secant path through bores in segments 110 or grooves along the sidewalls of segments 110). Moreover, in some embodiments, ligaments 36a and 36b may be lubricated to facilitate their movement with respect to segments 110.

The linking elements may be devised to accommodate the shapes and irregularities of the surfaces of the adjacent vertebrae. For example, in various embodiments the ligaments 36a and 36b may be configured with an elasticity that will allow the individual segments of the prosthesis 30 to move vertically with respect to one another when prosthesis 30 is in a closed position. Optionally, the ligaments 36a and 36b may be configured with an elasticity that will allow the segments 110a, 110b, and 110c to spread apart to adapt to any protuberance on a surface of either or both of the adjacent vertebrae.

Various embodiments may have one or more segments in which the height of a segment varies among different portions of the segment. Such variations may accommodate various shapes of the surfaces of the adjacent vertebrae. For example, segments 110a, 110b, and 110c of the embodiments illustrated in FIGS. 13A, 13B, and 15 have portions 112a, 112b, and 112c that are higher than portions 114a, 114b, and 114c.

Various embodiments may also have retainers to hold the ligaments. The embodiment illustrated in FIGS. 13A and 13B includes retainers in the form of the stoppers 116a and 116b. The stoppers 116a and 116b are disposed along ligaments 36a and 36b, respectively, and are sized to lodge into channels 120a and 120b, respectively (see FIG. 15) to retain or lock prosthesis 30 in a closed position. Stoppers can be used to secure each end of ligaments 36a and 36b, or one end of each ligament may be secured with a stopper 116 and the other directly fastened to a segment, such as shown for example with respect to segment 110c in FIGS. 13B and 15. An enlarged view of a stopper 116 in accordance with various embodiments is shown in FIG. 14. Other suitable types of stoppers, plugs, clips, latches, catches, locks, pawls, and dogs may also be employed as retainers. In addition, retainers may be used to lock other described prosthesis embodiments in addition to the one illustrated in FIGS. 13A, 13B, and 15.

Figure 16:
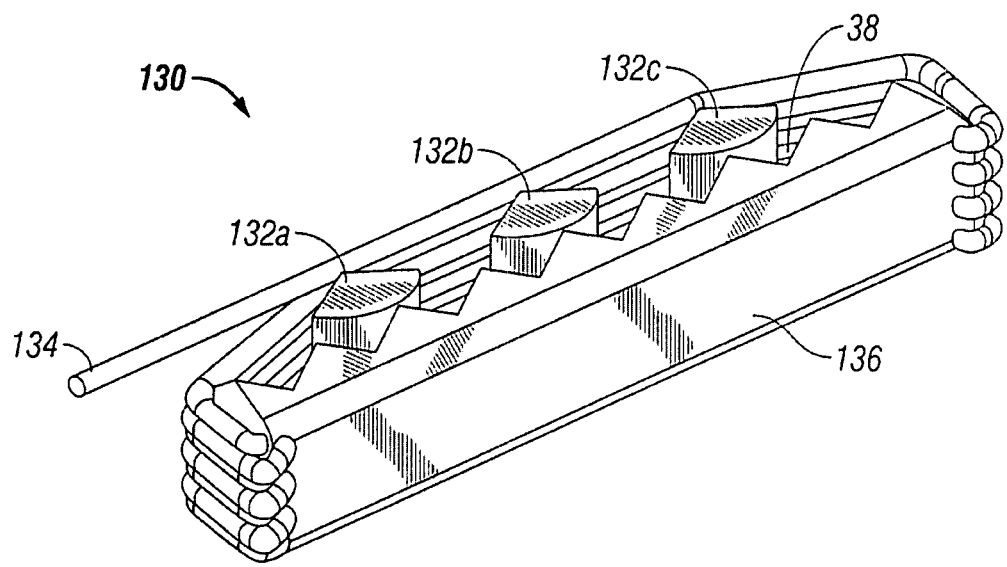
FIG. 16 is a perspective view of an exemplary nucleus prosthesis in accordance with some embodiments.

FIG. 16 is a perspective view of an nucleus prosthesis 130 in accordance with various embodiments. Prosthesis 130 includes segments 132a, 132b, and 132c, ligament 134, and strip 136 (comprising, in some embodiments, a track for the sliding of hinges as described later). Segments 132 may be substantially similar in material and shape to segments 32, 70, 90, and 110 described above. In other words, segments 132 are shaped such that when closed together (see FIG. 20), segments 132 form a disc shape, as described above. Further, the height and width of segments 132 may be selected with respect to the dimensions of the patient's disc 14 or the intervertebral disc space. Ligament 134 is substantially similar to ligament 36, also described above. As shown, ligament 134 may be threaded lengthwise back and forth between the ends of strip 136.

In the embodiment illustrated in FIG. 16, the strip 136 preferably is configured to bend or flex around segments 132 as segments 132 are brought together into a closed position. The strip 136 can comprise a flexible material, with an elasticity similar to or different from the elasticity of the segments or can have a gradient of elasticity. The strip can have recesses or voids, for example such as notches 38 shown in FIG. 16, that facilitate bending or flexing of the strip 136. Notches 38 optionally may open along the inward side of the strip as illustrated in FIG. 16, or open along the outward side of the strip. Optionally, the notches may not open along the inward or outward sides of the strip. The strip 136 also may be formed from a material having sufficient flexibility to accommodate the required bending or flexing without any notches or recesses. In various embodiments, strip 136 is bent by tightening the ligament 134.

Figure 17:
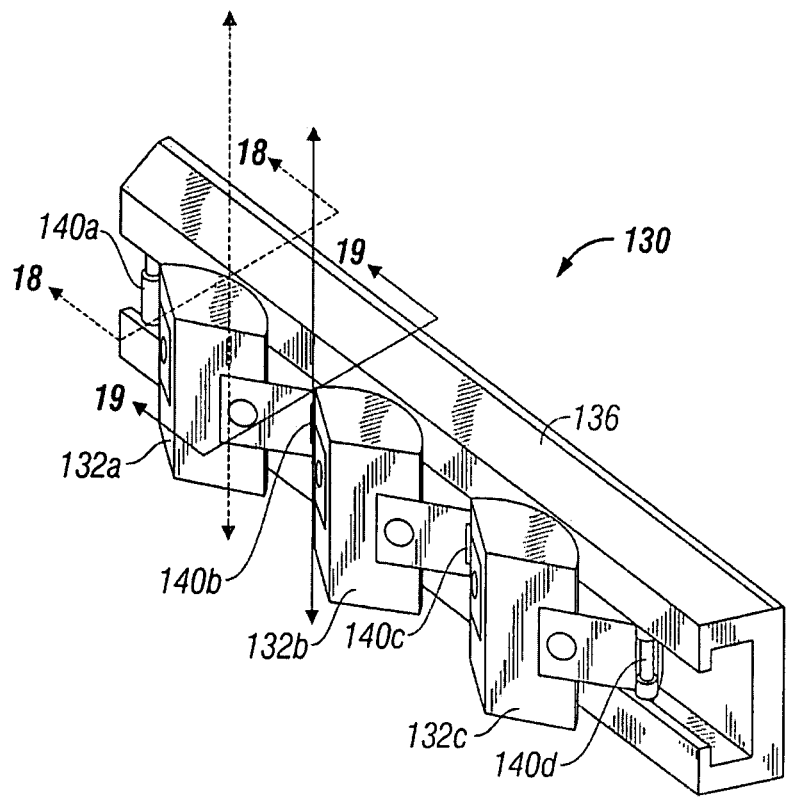
FIG. 17 is a perspective view of an exemplary nucleus prosthesis in accordance with some embodiments.

FIG. 17 is a partial perspective view of another embodiment of prosthesis 130. For ease of illustration, ligament 134 is omitted from FIG. 17. Segments 132a, 132b, and 132c are linked together by hinges 140b and 140c and are coupled to strip 136 by hinges 140a, 140b, 140c, and 140d. As illustrated, each of the hinges 140b and 140c is coupled to one or more of the segments 132 to form a serial line of segments. Each of the hinges 140 also may have a pin that rides within a groove 142 of strip 136, for example forming a track guiding the hinges. For example, in this embodiment hinge 140b is coupled between segments 132a and 132b and rides in groove 142, and hinge 140c is coupled between segments 132b and 132c and rides in groove 142. Hinge 140a is coupled to segment 132a alone, hinge 140d is coupled to segment 132c alone, and each of hinges 140a and 140d rides within groove 142. In alternate embodiments, other mechanism may be employed to couple segments 132 to strip 136.

Figure 18:
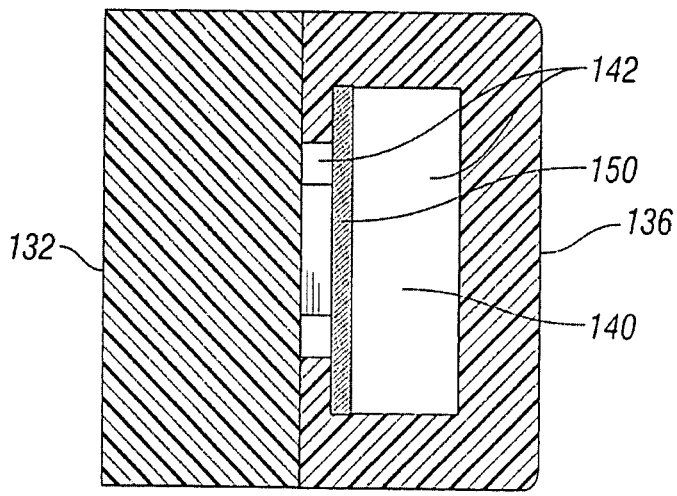
FIG. 18 is a cross-sectional view of the exemplary nucleus prosthesis of FIG. 17 in accordance with some embodiments.
Figure 19:
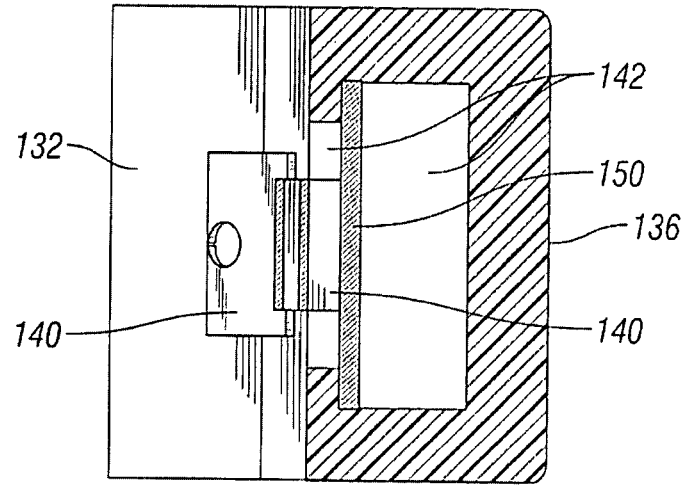
FIG. 19 is another cross-sectional view of the exemplary nucleus prosthesis of FIG. 17 in accordance with some embodiments.

Cross-sectional views along the cut-lines shown in FIG. 17 are shown in FIGS. 18 and 19. In particular, FIGS. 18 and 19 highlight the spatial relationships between segments 132, hinges 140, and groove 142. FIG. 18 illustrates a cross-sectional view of prosthesis 130 through one of the segments 132, and FIG. 19 illustrates a cross-sectional view of prosthesis 130 through one of the hinges 140. As shown in FIGS. 18 and 19, hinge 140 includes a pin 150 that rides within groove 142. As such, segments 132 are able to move freely within groove 142. In alternate embodiments, one or more of segments 132 each may be equipped with a pin 150 coupled to the strip 136. In various embodiments, hinges 140 may not have pins, and pins deployed with segments 132 may be the sole means of retaining the segments 132 with the strip 136. Other forms of retainers may be used instead of pins; for example, either or both of the segments 132 and the hinges 140 may be configured with integral or attached dovetail extensions that fit a dovetail channel in the strip 136. Other forms of extensions may also be used as a retainer, such as for example "T" shaped extensions integral with or attached to either or both of the segments 132 and the hinges 140, which fit a "T" shaped channel in the strip 136.

Figure 20:
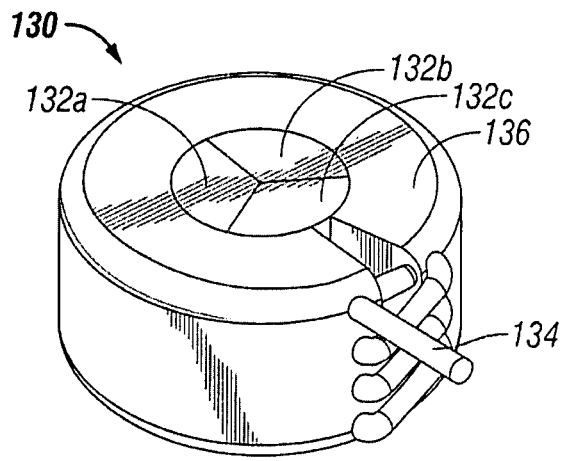
FIG. 20 is a perspective view of an exemplary nucleus prosthesis in accordance with some embodiments.
Figure 21:
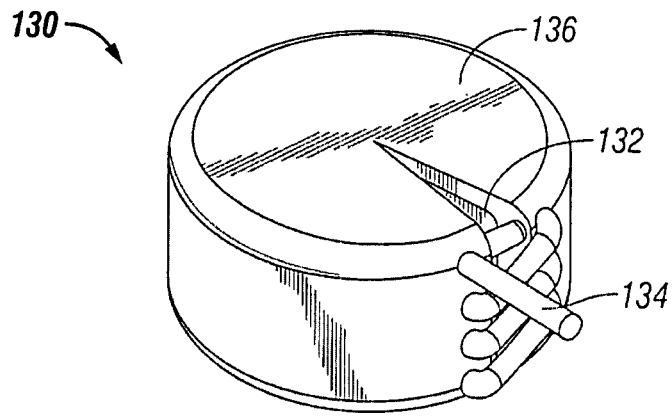
FIG. 21 is a perspective view of an exemplary nucleus prosthesis in accordance with some embodiments.

As mentioned above, prosthesis 130 is configured to close so that segments 132 form a disc shape. In particular, like prosthesis 30 described above, prosthesis 130 may be surgically introduced into the annulus fibrosus 16 in an open position and then bent to a closed position as it enters the disc. In various embodiments, prosthesis 130 is bent by pulling on ligament 134. FIG. 20 illustrates prosthesis 130 in a closed position. As shown, strip 136 encircles segments 132 holding them in a closed position. Prosthesis 130 may then be secured in a closed position by securing ligament 134 so that it holds the ends of the strip in proximity with each other. FIG. 21 illustrates an alternate embodiment of prosthesis 130 in which strip 136 generally encloses segments 132. For example, in this embodiment, the upper and lower surfaces of strip 136 may extend over segments 132. Alternatively, the groove 142 may also be enlarged to enclose segments 132.

Figure 22:
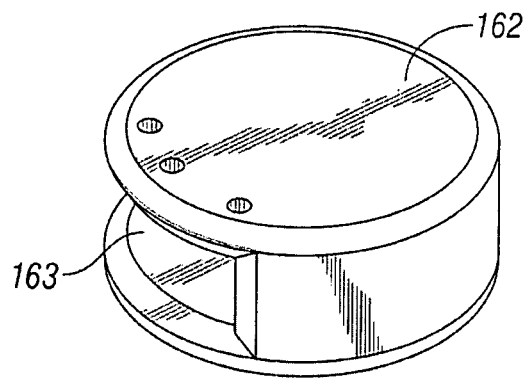
FIG. 22 is a perspective view of an exemplary enclosure in accordance with some embodiments.

FIG. 22 depicts an enclosure 162 that may be used with various embodiments of the prosthesis. Enclosure 162 may be configured in a disc shape and may be configured to enclose a prosthesis, such as prosthesis 30 or 130 or another suitable nucleus prosthesis. Each of the upper and lower surfaces of enclosure 162 can be generally flat, convex, or concave throughout the surfaces or in selected portions of the surfaces (as mentioned previously for the prosthesis). Enclosure 162 may be made from any suitable biocompatible material, such as Dacron® polyester fiber, other polymers or plastics, or other suitable materials. In various embodiments, a thickness, weave, or elasticity of enclosure 162 is selected to produce a desired stiffness. The stiffness in various embodiments may be sufficient for the enclosure 162 to have a normal shape, such as a disc shape, when external forces are not acting on the enclosure 162. In some embodiments, the enclosure 162 will have an elasticity and/or stiffness that tend to return the enclosure 162 to its normal shape when forces deforming the enclosure 162 cease. Alternatively, an enclosure 162 may not have a well defined shape, for example in embodiments of an enclosure comprising bag, such as a fabric sack for example.

Figure 23:
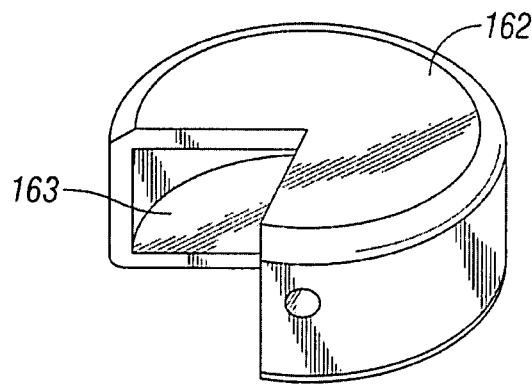
FIG. 23 is a perspective view of an exemplary enclosure in accordance with some embodiments.
Figure 24:
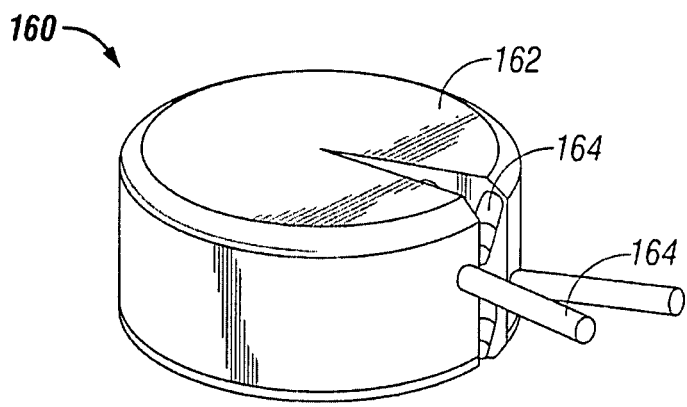
FIG. 24 is a perspective view of an exemplary nucleus prosthesis assembly in accordance with some embodiments.

FIG. 24 is a perspective view of a prosthesis assembly 160 in accordance with various embodiments. Prosthesis assembly 160 includes an enclosure 162, such as shown in FIG. 23, that holds a nucleus prosthesis, for example such as nucleus prosthesis 30 or 130 as described above, and a ligament 164 that can be used to close enclosure 162.

Figure 25:
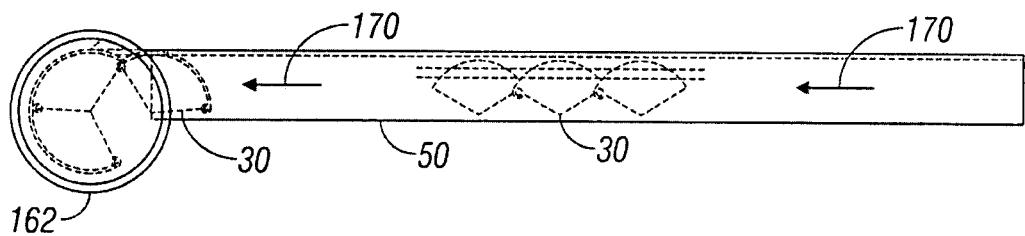
FIG. 25 is an obverse cross-sectional view of an exemplary prosthesis being inserted into an enclosure in accordance with some embodiments.

FIG. 25 illustrates a surgical implantation of prosthesis assembly 160 in accordance with some embodiments. The enclosure 162 may be coupled with an insertion instrument, for example such as the illustrated chute 50. The enclosure and the insertion instrument may be provided to the surgeon assembled in various embodiments. In some embodiments, after a surgical incision is made into the annulus fibrosus, enclosure 162 is fitted onto one end of chute 50 and may be placed into the annulus fibrosus 16.

In various other embodiments, the enclosure may be provided separately from the insertion instrument. In some embodiments, after a surgical incision is made into the annulus fibrosus, an insertion instrument such as chute 50 is put into place and an enclosure 162 is compressed or folded and fed through the chute 50 into the nucleus area.

Once inside the annulus fibrosus 16 or the intervertebral disc space, in various embodiments enclosure 162 may return generally to its normal shape. Although the embodiment illustrated in FIG. 25 depicts a particular embodiment of prosthesis 30, any other suitable prosthesis configuration may be used, such as for example prosthesis 130 or any variants of prostheses 30 and 130. Enclosure 162 preferably will have an interior compatible with the closed position of the nucleus prosthesis 30. In an advantageous embodiment, the enclosure 162 may be fitted onto an end of the chute 50 and thus maintained open while it is placed inside the annulus or the disc space, so as to facilitate the entrance of the prosthesis inside the enclosure afterwards. As illustrated in FIG. 25, the prosthesis 30 is fed in an open position through chute 50 in direction 170 into the enclosure 162, which is now inside the annulus fibrosus 16. As prosthesis 30 enters the enclosure 162, it folds until the prosthesis 30 is in a closed position. The prosthesis 30 may also be tightened into a closed position with the ligament 36. After prosthesis 30 is inserted and folded into a closed position, enclosure 162 may be closed with ligament 164, for example by pulling it. Next, ligament 164 may be trimmed, chute 50 removed, and the surgical incision closed. In alternate embodiments, prosthesis assembly 160 may be employed as a replacement for a disc 14 that been removed during a complete discectomy.

In various embodiments, the use of an insertion instrument may have advantageous. For example, in embodiments in which enclosure 162 does not have sufficient stiffness for the enclosure 162 to have a normal shape, an insertion instrument may be used to hold the enclosure open and/or in place during the insertion of the prosthesis. For example, FIG. 26 illustrates an embodiment of an enclosure comprising a fabric sack 162. The end of the chute 50 holds the enclosure 162 open and retains the enclosure 162 in place during insertion of the prosthesis. The prosthesis may be passed through channel 51 with segments 32a, 32b, and 32c arranged in a serial line to enter the enclosure 162. In the illustrated embodiment, segment 32c encounters the deflector 53 first, causing the segment to turn and commencing the closure of the segments 32a, 32b, and 32c. In various embodiments, lateral manipulation of the end of the leading segment (e.g., segment 32c in FIG. 26) may facilitate closure, for example as illustrated in FIG. 26 in which the end of segment 32c is moved toward the outer lateral wall of the channel 51 comprising the deflector 53 (which is the top wall of channel 51 in the orientation shown in FIG. 26), causing the hinge between segments 32c and 32b to move toward the inner lateral wall of the channel 51 (which is the bottom wall of channel 51 in the orientation shown in FIG. 26), which in turn causes the hinge between segments 32b and 32a to move toward the upper wall of the channel 51, thereby placing segments 32b and 32a in a better position for closure of those segments as shown in FIG. 27.

In various embodiments, the prosthesis may be deployed with other spinal stabilization structures. For example, FIG. 28 depicts an embodiment in which the prosthesis 30 is configured as a fusion device and is implanted within nucleus fibrosus 16 as discussed above, although other prosthesis embodiments and implantation methods may be used. For this embodiment and others, a posterior spinal stabilization device can be used to provide additional stability to the intervertebral alignment. In the illustrated embodiment, a pedicle screw 81 is implanted in each of the vertebrae 12a and 12b. In preferred embodiments, the pedicle screws 81 advantageously can be configured as described in U.S. application Ser. No. 10/473,999 filed Apr. 12, 2004 (FR2823093), or U.S. application Ser. No. 10/498,234 filed Dec. 7, 2004 (FR2833151), both of which are commonly owned by the assignee of the present application, and both of which are incorporated herein by reference. The bar 82 is fixed to each screw 81 and tends to hold the vertebrae 12a and 12b in the alignment determined by the surgeon during surgery. As those of skill in the art will recognize after appreciating this disclosure, other spinal fixation devices alternatively may be used.

Flexible vertebral stabilization devices may also be deployed with a prosthesis. For example, FIG. 29 depicts an embodiment using a vertebral support device as described in U.S. application Ser. No. 11/672,745 filed Feb. 8, 2007, (FR 0611198) which is commonly owned by the assignee of the present application, and which is incorporated herein by reference. In the illustrated embodiment, a pedicle screw 81 is implanted in each of the vertebrae 12a and 12b. A linking element 83 comprises a dampening element 84 and rigid elements 85 articulated by the dampening element 84. Each of the rigid elements 85 is fixed to one of the pedicle screws 81, respectively. The vertebral support device provides flexible articulation of the rigid elements 85, which may provide some freedom of movement to the vertebrae 12a and 12b. In various embodiments, the dampening element 84 accommodates the stresses experienced by the linking element 83 during these movements, and tends to return the vertebrae 12a and 12b to an intended configuration.

In some embodiments, multiple prostheses may be deployed within the annulus fibrosus 16 or the intervertebral disc space. For example, FIG. 30 depicts an embodiment using two prostheses 30 appropriately sized for insertion within the annulus fibrosus or for deployment within the intervertebral disc space following a complete discectomy. Other embodiments may use more than two prostheses. Other prosthesis embodiments may be used, and combinations of prosthesis embodiments may be used. An enclosure may be used with one, several, or all of the various prostheses used in a multiple-prosthesis embodiments. Multiple-prosthesis embodiments also may be used with other spinal stabilization structures, such as those discussed above.

Various embodiments may be configured to mitigate or impose lordosis or kyphosis. For example, FIG. 31 depicts an embodiment of a nucleus prosthesis 30 implanted within the annulus fibrosus and configured to mitigate or impose lordosis. The upper and lower surfaces of the depicted prosthesis 30 are angled so that the anterior portion of the prosthesis 30 is thinner than the posterior portion. A kyphotic condition could be mitigated or imposed by configuring a prosthesis having an anterior portion that is thicker than the posterior portion. After appreciating the disclosure of the present application, those of skill in the art will recognize that many different embodiments of prostheses in accordance with the invention may optionally be configured to mitigate or impose lordosis or kyphosis.

Those of skill in the art will recognize after appreciating this disclosure that the steps of the various methods, processes, and other techniques disclosed herein need not be performed in any particular order, unless otherwise expressly stated or logically necessary to satisfy expressly stated conditions. In addition, after appreciating this disclosure those skilled in the art will recognize that the invention may be embodied in a variety of different forms and that various changes, substitutions, and alterations can be made without departing from the spirit and scope of the invention. References herein to surfaces or other structures as "upper," "top," "lower," "bottom," or having a "height," "width," or "length," and directional references such as "horizontal" and "vertical," are generally arbitrary and for convenience only, and those of skill in the art will recognize after appreciating this disclosure that such designations appropriately may be reoriented in particular embodiments. The described embodiments are illustrative only and are not restrictive, and the scope of the invention is defined solely by the following claims.

The invention claimed is:

1. A nucleus prosthesis comprising:
 a plurality of segments, including a leading segment and a trailing segment each having a leading face, a trailing face, and an external face; and
 a ligament coupling the segments,
 the prosthesis having:
 an open position in which the segments are disposed along the ligament in a serial line with the leading segment at an end of the serial line and the trailing segment at another end of the serial line; and
 a closed position in which the segments are disposed to form a disc shape with the leading face of the leading segment and the trailing face of the trailing segment substantially apposed and the external faces of the leading segment and the trailing segment disposed along the exterior circumference of the disk shape with the ligament entering and exiting the leading segment at least through openings on the external face of the leading segment and entering and exiting the trailing segment at least through openings on the external face of the trailing segment.

2. The prosthesis of claim 1 in which one or more of the segments are elastic.

3. The prosthesis of claim 2 in which one or more of the segments has an inner portion having a first elasticity and an outer portion having a second elasticity.

4. The prosthesis of claim 2 in which at least one of the segments has an elasticity gradient within said segment.

5. The prosthesis of claim 1, comprising a closure element on an end of the ligament.

6. The prosthesis of claim 5, in which the closure element is configured to engage another end of the ligament, with such engagement configured to urge the prosthesis into a closed position.

7. The prosthesis of claim 1, comprising a retainer disposed along the ligament and configured to hold the segments in the disc shape.

8. The prosthesis of claim 1 in which the ligament takes a secant path through at least one of the leading and trailing segments using openings on the external face.

9. The prosthesis of claim 1, comprising a strip to which one or more of the segments are coupled.

10. The prosthesis of claim 9 in which one or more segments are coupled to the strip by a pin located in a channel of the strip.

11. The prosthesis of claim 9 in which a hinge between two of the segments is coupled to the strip by a pin located in a channel of the strip.

12. The prosthesis of claim 9 in which the strip is configured to fold around the segments.

13. The prosthesis of claim 12 in which the strip is configured to enclose the generally cylindrical shape.

14. The prosthesis of claim 9, comprising a ligament coupled to the strip and configured to fold the strip when a pulling force is applied to the ligament.

15. The prosthesis of claim 9, in which the strip comprises a track.

16. The prosthesis of claim 1 in which the prosthesis is a fusion device.

17. A nucleus prosthesis comprising:
 at least three linked segments coupled together serially in a line when the prosthesis is in an open position and configured such that a first segment in the line is generally adjacent to a face of a last segment in the line when the prosthesis is in a closed position with each of the segments having an exterior surface forming part of an outer surface of the prosthesis in the closed position; and
 a ligament configured to couple the segments together in the closed position, with the ligament entering and exiting the exterior surface of each of the segments, wherein the exterior surface of each segment is disposed on an exterior circumference of the device in the closed position.

18. The prosthesis of claim 17 in which the face of the first segment comprises a male interlocking element and the face of the last segment comprises a female interlocking element configured to connect to the male interlocking element.

19. The prosthesis of claim 18 in which the male interlocking element and the female interlocking element are configured to enable the segments to move vertically with respect to one another.

20. The prosthesis of claim 17 in which the face of the first segment comprises a female interlocking element and the face of the last segment comprises a male interlocking element configured to connect to the female interlocking element.

21. The prosthesis of claim 20 in which the male interlocking element and the female interlocking element are configured to enable the segments to move vertically with respect to one another.

22. The prosthesis of claim 17 in which the face of the first segment comprises a female interlocking element and the face of the last segment comprises a male interlocking element configured to connect to the female interlocking element.

23. The prosthesis of claim 22 in which the male interlocking element and the female interlocking element are configured to enable the segments to move vertically with respect to one another.

24. The prosthesis of claim 17 in which the face of the first segment comprises a male interlocking element and the face of the last segment comprises a female interlocking element configured to connect to the male interlocking element.

25. The prosthesis of claim 24 in which the male interlocking element and the female interlocking element are configured to enable the segments to move vertically with respect to one another.

26. The prosthesis of claim 17, comprising a plurality of ligaments traversing the segments.

27. A nucleus prosthesis comprising at least three linked segments coupled together by one or more hinges in a serial alignment when the segments are in an open position, the segments configured so that a first implanted segment is generally adjacent to a last implanted segment when the segments are in a closed position with each of the segments having an exterior surface forming part of an outer surface of the prosthesis in the closed position, and a ligament configured to couple the segments together in the closed position, with the ligament entering and exiting the exterior surface of each of the segments, wherein the exterior surface of each segment is disposed on an exterior circumference of the device in the closed position.

* * * * *